(12) United States Patent
Riveroll et al.

(10) Patent No.: US 12,116,565 B2
(45) Date of Patent: Oct. 15, 2024

(54) METHODS OF PRODUCING ALGAL CELL CULTURES AND BIOMASS, LIPID COMPOUNDS AND COMPOSITIONS, AND RELATED PRODUCTS

(71) Applicant: SOLARVEST BIOENERGY INC., Vancouver (CA)

(72) Inventors: Angela Lynne Riveroll, Vancouver (CA); Raymond Surzycki, Bloomington, IN (US); Michael Daniel McDougall, Vancouver (CA); Nancy Grant, Vancouver (CA); Kylie Muio, Vancouver (CA); Hayley Michelle McKenna, Vancouver (CA)

(73) Assignees: SOLARVEST BIOENERGY INC., Vancouver (CA); SOLARVEST PEI INC., Vancouver (CA)

( * ) Notice: Subject to any disclaimer, the term of this patent is extended or adjusted under 35 U.S.C. 154(b) by 0 days.

(21) Appl. No.: 14/896,809

(22) PCT Filed: Jun. 12, 2014

(86) PCT No.: PCT/IB2014/001043
§ 371 (c)(1),
(2) Date: Dec. 8, 2015

(87) PCT Pub. No.: WO2014/199220
PCT Pub. Date: Dec. 18, 2014

(65) Prior Publication Data
US 2016/0122706 A1 May 5, 2016

Related U.S. Application Data

(60) Provisional application No. 61/834,398, filed on Jun. 12, 2013.

(51) Int. Cl.
| | | |
|---|---|---|
| *C12N 1/12* | (2006.01) | |
| *A23L 17/00* | (2016.01) | |
| *A23L 17/60* | (2016.01) | |
| *A61K 8/36* | (2006.01) | |
| *A61K 31/202* | (2006.01) | |
| *A61K 36/02* | (2006.01) | |
| *C11B 5/00* | (2006.01) | |
| *C11C 1/00* | (2006.01) | |
| *C12P 7/64* | (2022.01) | |
| *C12P 7/6427* | (2022.01) | |
| *C12P 23/00* | (2006.01) | |

(52) U.S. Cl.
CPC .............. *C12N 1/12* (2013.01); *A23L 17/00* (2016.08); *A23L 17/60* (2016.08); *A61K 8/361* (2013.01); *A61K 31/202* (2013.01); *A61K 36/02* (2013.01); *C11B 5/0085* (2013.01); *C11C 1/00* (2013.01); *C12P 7/64* (2013.01); *C12P 7/6427* (2013.01); *C12P 23/00* (2013.01); *A23V 2002/00* (2013.01)

(58) Field of Classification Search
CPC ........ C12N 1/12; A61K 8/361; A61K 31/202; C12P 7/6427; A23V 2002/00
USPC ............................................................ 426/7
See application file for complete search history.

(56) References Cited

U.S. PATENT DOCUMENTS

| | | | |
|---|---|---|---|
| 9,375,703 B2 * | 6/2016 | Harlin | ................ B01J 20/28033 |
| 9,434,967 B2 | 9/2016 | Liu et al. | |
| 2005/0037480 A1 * | 2/2005 | Chiueh | ................... C12N 1/12 |
| | | | 435/252.1 |
| 2009/0211150 A1 | 8/2009 | Wu et al. | |
| 2009/0298159 A1 | 12/2009 | Wu et al. | |
| 2011/0250178 A1 * | 10/2011 | Brooks | .................. C12N 1/125 |
| | | | 424/195.17 |
| 2012/0088278 A1 | 4/2012 | Kim et al. | |
| 2012/0128851 A1 * | 5/2012 | Brooks | ................. A23K 10/16 |
| | | | 426/549 |
| 2015/0210976 A1 | 7/2015 | Akashi et al. | |

FOREIGN PATENT DOCUMENTS

| | | |
|---|---|---|
| AU | 2021200394 A1 | 3/2021 |
| CN | 101445815 A | 6/2009 |
| CN | 101555454 B | 10/2009 |
| CN | 101875904 A | 11/2010 |
| CN | 102465098 A | 5/2012 |
| EP | 1889599 A1 | 2/2008 |
| JP | S4936884 A | 4/1974 |
| JP | S5234975 A | 3/1977 |
| JP | S5432690 A | 3/1979 |

(Continued)

OTHER PUBLICATIONS

Rapisarda, P. et al. 1999. J. Agric. Food Chem. 47: 4718-4723.*

(Continued)

*Primary Examiner* — Hamid R Badr

(57) ABSTRACT

The present invention is directed to methods of producing algal biomass and algal cell cultures, and lipid compounds and compositions thereof, including fatty acids, carotenoids and fat soluble vitamins. The present invention is further directed to methods of preparing related food products and industrial and pharmaceutical compositions. In various exemplary embodiments, the methods comprise growing algae in a juice based medium, including a medium that contains natural nitrogen or a medium that is free of chemical additives and preservatives, to produce algal cell cultures, algal biomass, algae derived lipid compounds and compositions, and related products, all that can be certified organic.

15 Claims, 14 Drawing Sheets

(56) References Cited

FOREIGN PATENT DOCUMENTS

| | | |
|---|---|---|
| JP | S6368077 A | 3/1988 |
| JP | H03254674 A | 11/1991 |
| JP | 2013027344 A | 2/2013 |
| JP | 2013039085 A | 2/2013 |
| JP | 2020185012 A | 11/2020 |
| KR | 20210028279 A | 3/2021 |
| KR | 20230119731 A | 8/2023 |
| WO | 2004036982 A2 | 5/2004 |
| WO | 2004082399 A | 9/2004 |
| WO | 2007061845 A2 | 5/2007 |
| WO | 2008083453 A1 | 7/2008 |
| WO | 2008134836 A2 | 11/2008 |
| WO | 2008151149 A2 | 12/2008 |
| WO | 2008154294 A1 | 12/2008 |
| WO | 2010081335 A1 | 7/2010 |
| WO | 2011090730 A1 | 7/2011 |
| WO | 2012153955 A | 11/2012 |
| WO | 2012175027 A2 | 12/2012 |
| WO | 2013013210 A1 | 1/2013 |

OTHER PUBLICATIONS

Miller, N. J. et al. Food Chem. 60: 331-337 (1997) (Year: 1997).*
SHarker, M. G. U. et al. J. Bangladesh Agric. Univ. 5: 117-128 (2007) (Year: 2007).*
Alberti, A. et al. Barz. Arch. Biol. Technol. 54: 551-558 (2011) (Year: 2011).*
Yan, D. et al. Biores. Biotechnol. 102: 6487-6493 (2011) (Year: 2011).*
European Extended Search Report dated Mar. 31, 2017 for European counterpart patent application EP14810557.0.
Nakai, S. et al., "Algal Growth Inhibition Effects and Inducement Modes by Plant-Producing Phenols", Wat. Res. vol. 35, No. 7, pp. 1855-1859, 2001.
Toyub et al, "Change in Some Chemical Parameters of Two Environment Polluting Waster (Fertilizer Factory Effluent and Sweetmeat Factory Waste) Media After Culture of Three Important Microalgae", Bangladesh J. Sci. Ind. Res. 42(3), 299-310, 2007, 12 pages.
Gharras H., "Polyphenols: Food Sources, Properties and Applicantions—A Review", Int'l. J. of Food Sci. and Tech. 2009, 44, 2512-2518; 7 pages.
Cheng, Yun, et al. "Biodiesel production from Jerusalem artichoke (*Helianthus tuberosus L.*) tuber by heterotrophic microalgae *Chlorella protothecoides*." Journal of Chemical Technology & Biotechnology: International Research in Process, Environmental & Clean Technology 84.5 (2009): 777-781.
Christiansen, Andrew P. et al. "Forms of Nitrogen in the Soil", Soils Home Study Course, University of Nebraska Cooperative Extension, Institute of Agriculture and Natural Resources, 1999: https://passel2.unl.edu/view/lesson/3176eba1ba31/2.
De Swaaf, Martin E., et al. "High-cell-density fed-batch cultivation of the docosahexaenoic acid producing marine alga *Crypthecodinium cohnii*." Biotechnology and bioengineering 81.6 (2003): 666-672.
Elsanhoty, Rafaat M., et al. "Screening of medium components by Plackett-Burman design for carotenoid production using date (*Phoenix dactylifera*) wastes." Industrial Crops and Products 36.1 (2012): 313-320.
European Chemicals Bureau (2004). "European Union Risk Assessment Report—EDTA", Institute for Health and Consumer Protection, vol. 141, Google Scholar.
Fujita, Tomoya, et al. "Effect of mixed organic substrate on $\alpha$-tocopherol production by *Euglena gracilis* in photoheterotrophic culture." Applied microbiology and biotechnology 79 (2008): 371-378.
Glibert, Patricia M., et al. "Escalating worldwide use of urea—a global change contributing to coastal eutrophication." Biogeochemistry 77 (2006): 441-463.
Gross, Wolfgang, and Claus Schnarrenberger. "Heterotrophic growth of two strains of the acido-thermophilic red alga *Galdieria sulphuraria*." Plant and cell physiology 36.4 (1995): 633-638.
Gupta, V. K., et al. "Removal of ammonium ions from wastewater a short review in development of efficient methods." (2015): 149-158.
Hollyer, James, et al. "The allowed use of commercial fertilizers, pesticides, and synthetic substances on US farms under the USDA National Organic Program." Food Safety and Technology (2013): 1-9.
Hong, Won-Kyung, et al. "Production of lipids containing high levels of docosahexaenoic acid by a newly isolated microalga, *Aurantiochytrium sp.* KRS101." Applied biochemistry and biotechnology 164 (2011): 1468-1480.
Iwe, Madu O., and Ann N. Agiriga. "Production and evaluation of Ighu from selected cassava varieties using a motorized shredder—a response surface analysis." Food science & nutrition 1.6 (2013): 464-473.
Kajikawa, Masataka, et al. "A front-end desaturase from *Chlamydomonas reinhardtii* produces pinolenic and coniferonic acids by $\omega$13 desaturation in methylotrophic yeast and tobacco." Plant and cell physiology 47.1 (2006): 64-73.
Kemmei, Tomoko, et al. "Determination of ethylenediaminetetraacetic acid in sea water by solid-phase extraction and high-performance liquid chromatography." Analytica chimica acta 709 (2012): 54-58.
Kester, Dana R., et al. "Preparation of artificial seawater 1." Limnology and oceanography 12.1 (1967): 176-179.
Kim, Kyochan, et al. "A novel fed-batch process based on the biology of *Aurantiochytrium sp.* KRS101 for the production of biodiesel and docosahexaenoic acid." Bioresource technology 135 (2013): 269-274.
Lim, David KY, et al. "Isolation and evaluation of oil-producing microalgae from subtropical coastal and brackish waters." PLoS One 7.7 (2012): e40751.
Lu, Yue, et al. "Biodiesel production from algal oil using cassava (*Manihot esculenta* Crantz) as feedstock." Journal of Applied Phycology 22 (2010): 573-578.
Martinez-Goss, M. R. "6th Asia-Pacific Conference on Algal Biotechnology (APCAB)", "Makati City, Philippines, Oct. 12-15, 2006 Guest Editors Milagrosa R. Martinez-Goss Institute of Biological Sciences, University of the Philippines Los Baños, Philippines Marco Nemesio E. Montaño Marine Science Institute, College of Science, University of the Philippines, Diliman, Quezon City, Philippines Anicia Q. Hurtado Integrated Services for the Development of Aquaculture and Fisheries (ISDA), Tabuc Suba, Iloilo City, Philippines Avigad . . . " Journal of Applied Phycology: Dec. 2007.
Morrison, Sarah. That beet is sweet!. Statistics Canada, 2008.
Nadir, N., et al. "Comparison of sweet sorghum and cassava for ethanol production by using *Saccharomyces cerevisiae*." Journal of Applied Sciences 9.17 (2009): 3068-3073.
Ogbonna, James C., et al. "Heterotrophic cultivation of *Euglena gracilis* Z for efficient production of $\alpha$-tocopherol." Journal of applied phycology 10 (1998): 67-74.
Pal, Dipasmita, et al. "The effect of light, salinity, and nitrogen availability on lipid production by *Nannochloropsis sp*." Applied microbiology and biotechnology 90 (2011): 1429-1441.
Raposo, M. Filomena de J., et al. "On the utilization of microalgae for brewery effluent treatment and possible applications of the produced biomass." Journal of the Institute of Brewing 116.3 (2010): 285-292.
Shen, Y., et al. "Heterotrophic culture of *Chlorella protothecoides* in various nitrogen sources for lipid production." Applied Biochemistry and Biotechnology 160 (2010): 1674-1684.
Shi, Xian-Ming, et al. "Heterotrophic production of biomass and lutein by *Chlorella protothecoides* on various nitrogen sources." Enzyme and microbial technology 27.3-5 (2000): 312-318.
Takeyama, Haruko, et al. "Production of antioxidant vitamins, $\beta$-carotene, vitamin C, and vitamin E, by two-step culture of *Euglena gracilis* Z." Biotechnology and bioengineering 53.2 (1997): 185-190.

(56) References Cited

OTHER PUBLICATIONS

Tani, Yoshiki, and Haruhiko Tsumura. "Screening for tocopherol-producing microorganisms and α-tocopherol production by *Euglena gracilis* Z." Agricultural and biological chemistry 53.2 (1989): 305-312.
Thomas, S., 6th Asia-Pacific Conference on Algal Biotechnology, Abstract, (2006).
Unagul, Panida, et al. "Coconut water as a medium additive for the production of docosahexaenoic acid (C22: 6 n3) by *Schizochytrium mangrovei* Sk-02." Bioresource Technology 98.2 (2007): 281-287.
Wang, Hong, et al. "Total antioxidant capacity of fruits." Journal of agricultural and food chemistry 44.3 (1996): 701-705.
Wei, Aili, et al. "Effects of cassava starch hydrolysate on cell growth and lipid accumulation of the heterotrophic microalgae *Chlorella protothecoides*." Journal of Industrial Microbiology and Biotechnology 36.11 (2009): 1383.
Wen, Zhi-You, and Feng Chen. "Perfusion culture of the diatom *Nitzschia laevis* for ultra-high yield of eicosapentaenoic acid." Process Biochemistry 38.4 (2002): 523-529.
Wong, Ming-Hung, et al. "Food processing wastes as nutrient sources in algal growth." Hazardous and Industrial Waste Management and Testing: Third Symposium. No. 851. ASTM International, 1984.
Yamasaki, Takashi, et al. "Utilization of Shochu distillery wastewater for production of polyunsaturated fatty acids and xanthophylls using thraustochytrid." Journal of bioscience and bioengineering 102.4 (2006): 323-327.
Yoshida, Masaki, et al. "Proteomic comparison between interphase and metaphase of isolated chloroplasts of *Cyanidioschyzon merolae* (Cyanidiophyceae, Rhodophyta)." Phycological research 59.1 (2011): 1-15.
Adepoju, Oladejo Thomas, and Justina Oriaku Nwangwu. "Nutrient composition and contribution of noodles (abacha) and local salad from cassava (*Manihot* spp) to nutrient intake of Nigerian consumers." African Journal of Food Science 4.7 (2010): 422-426.
Anonymous, "Beans and Pulses in your Diet—Eat Well", NHS, May 21, 2018: https://web.archive.org/web/20190819041913/https://www.nhs.uk/live-well/eat-well/beans-and-pulses-nutrition/.
Anonymous, "Production of California Raisins", California Raisin Association: http://www.raisins-jp.org/process/production.html.
Anonymous, "Instant Ocean Sea Salt" MSDS product sheet, Pentair, Apr. 7, 2005: https://pentairaes.com/media/docs/IS50-160-200-MSDS-Sheet.pdf.
Bach, Vibe et al. "Sensory quality and appropriateness of raw and boiled Jerusalem artichoke tubers (*Helianthus tuberosus* L.)." Journal of the Science of Food and Agriculture 93.5 (2013): 1211-1218.
Bajpai, Pratima, and Argyrios Margaritis. "Production of high fructose syrup from Jerusalem artichoke tubers using *Kluyveromyces marxianus* cells immobilized in agar gel." The Journal of General and Applied Microbiology 31.4 (1985): 305-311.
Beman, Michael J., et al. "Agricultural runoff fuels large phytoplankton blooms in vulnerable areas of the ocean." Nature 434.7030 (2005): 211-214.
Chandrasekaran, M., and Ali H. Bahkali. "Valorization of date palm (*Phoenix dactylifera*) fruit processing by-products and wastes using bioprocess technology—Review." Saudi journal of biological sciences 20.2 (2013): 105-120.
Chaung, Kai-Chuang, et al. "Effect of culture conditions on growth, lipid content, and fatty acid composition of Aurantiochytrium mangrovei strain BL10." AMB Express 2.1 (2012): 1-11.
Cheng, Yun, et al. "Alga-based biodiesel production and optimization using sugar cane as the feedstock." Energy & Fuels 23.8 (2009): 4166-4173.

\* cited by examiner

METHODS OF PRODUCING ALGAL CELL CULTURES AND BIOMASS, LIPID COMPOUNDS AND COMPOSITIONS, AND RELATED PRODUCTS

CROSS-REFERENCE TO RELATED APPLICATIONS

This application is a U.S. national application under 37 C.F.R. § 371(b) of International Application Serial No. PCT/IB2014/001043 filed Jun. 12, 2014, which claims priority under 35 U.S.C § 119(e) to U.S. Provisional Application Ser. No. 61/834,398, filed on Jun. 12, 2013, each of which is incorporated herein by reference.

FIELD OF THE INVENTION

The present invention is directed to methods of producing algal biomass and cell cultures, and lipid compounds and compositions thereof, including fatty acids, carotenoids and fat soluble vitamins. The present invention is further directed to methods of preparing related food products and industrial and pharmaceutical compositions. In various exemplary embodiments, the methods comprise growing algae in a juice based medium, including a medium that is free of chemical additives and preservatives, to produce algal cell cultures, algal biomass, lipid compounds and compositions, and related products, all that can be certified organic.

BACKGROUND

Algae (both micro- and macro-algae) are a diverse group of organisms that inhabit most ecosystems on earth. Algae are most generally classified by pigment. Green algae or chlorophytes and contain chlorophyll a and b. Red algae or rhodophytes contain both chlorophyll a and phycobilins. Brown algae, known as chromophytes, contain chlorophyll a and c, but lack chlorophyll b.

Examples of algae species utilized in aquaculture include: *Nannochloropsis oculata* (2-4 μm), *Isochrysis galbana* (5-7 μm), *Schizochytrium* sp., *Tetraselmis chuii* (7-10 μm), Chaetoceros gracilis (6-8 μm), *Dunaliella tertiolecta* (7-9 μm), and several species of *Chlorella* (3-9 μm in diameter), *Nitzschia* and *Chlamydomonas*.

Chemical features of the aquatic environment play an important role in determining algal growth rates and biomass quality. In general, the composition of medium used to cultivate microalgae share several common features. Some nutrients must be supplied at relatively large concentrations. These nutrients, known as macronutrients, are carbon (C), nitrogen (N) phosphorous (P), sodium (Na), sulphur (S), potassium (K) and magnesium (Mg). Micronutrients, which are necessary at lower concentrations, must also be supplied. These micronutrients include manganese (Mn), zinc (Zn), copper (Cu), molybdenum (Mo) and cobalt (Co). Iron (Fe), chloride (Cl), calcium (Ca) and borium (Bo). These nutrients are required for algal growth. The molar stoichiometry of the macro- and micro-nutrients present in the algal culture medium is a critical feature of the medium and attention must be paid to these ratios when developing or improving media recipes.

As with all living organisms, a source of carbon that algae are capable of assimilating must be supplied to synthetic algal growth medium. Carbon supplied in the form of carbon dioxide is known as inorganic carbon. This carbon is fixed by the process of photosynthesisis. Some algal species can grow exclusively on inorganic carbon sources, and this growth mode is referred to as photoautotrophic growth. Most species of algae can assume a photoautotrophic growth mode. Some algae may also have the ability to obtain energy from organic carbon sources without the need for photosynthesis; this growth mode is referred to as a heterotrophic growth mode. Other algae can simultaneously utilize light and carbon dioxide as well as organic carbon sources for growth and this is referred to as mixotrophic growth. In the case of mixotrophic or heterotrophic growth modes, carbon sources for cultures of microalgae include glucose, dextrose, acetate and methanol (a source reduced carbon).

Common sources of nitrogen supplemented to algal growth medium are nitrate ($NO_3$), nitrite ($NO_2$), ammonium ($NH_4$), urea, amino acids (monosodium glutamate or arginine), tryptone, peptone, casein, non-organic yeast extract and corn steep liquor.

Phosphorus, sulfur and magnesium are all essential macronutrients the addition of which is required for algal growth. Sulfate ($SO_4$) is the form of sulfur that is generally added to a synthetic algal growth media. Inorganic phosphate ($H_2PO4$ or $HPO_4$) is the form of phosphorus that is generally provided to algal culture medium; however, forms of organic phosphate may also be used. The excess of phosphate has been linked to algal blooms in both freshwater and marine ecosystems.

Iron is a key element that plays an important role in cellular metabolism and energy production in the algal cell. In general, ferric and ferrous forms of iron are readily assimilated by microalgae. Early attempts at supplementing iron often resulted in the precipitation of the iron out of solution. Therefore, many recipes require iron to be suspended in a chemical chelating agent, usually sodium ethylenediaminetetracetic acid (EDTA). EDTA chelates other trace elements such as copper, cobalt, and cadmium.

Other elements referred to as trace elements must be supplemented to synthetic algal culture media. Copper, manganese, molybdenum, and zinc are the metals usually included in solutions of trace elements. Vanadium, boron, and cobalt are sometimes included in trace elements, as well. Supplementation with high concentrations of these metals is toxic and therefore care must be taken to not add them in excess. The addition of chemical chelators such as EDTA to solutions containing these metals is often employed to prevent precipitation.

It has been demonstrated that the addition of vitamins can change the fatty acid composition of *Schizochytrium* and improve the biomass output of other species of algae. Therefore, many formulation of synthetic growth medium include added vitamins.

One commercial application of algae is their ability to produce commercially valuable lipid and lipophilic compounds, such as various fatty acids and antioxidants. Omega-3 fatty acids, for example, are important nutrients for physical and mental health. These essential fatty acids support cardiovascular, reproductive, immune and nervous system health. Omega-3 fatty acids are highly concentrated in the brain and appear to be important for cognitive (brain-memory and performance) and behavioral function. In fact, infants who do not get enough omega-3 fatty acids from their mothers during gestation are at risk for developing vision and nerve conditions.

Thraustochytrids are microalgae that have been the focus of significant research and development with regard to the production of omega-3 fatty acids. Thraustochytrids are known to synthesize and accumulate polyunsaturated fatty acids (PUFA), such as docosahexaenoic acid (DHA; $C_{22:6}$ n-3). Industrial production of DHA from Thraustochytrids has advanced considerably in the past two decades. The key features that lead to economic production of DHA from these species of algae was their ability to grow in heterotrophic growth medium. Formulations of heterotrophic medium that included glucose as a carbon source and MSG, corn steep liquor or yeast extract as a nitrogen source produced high cell concentration, fast growth rates and significant quantities of DHA when grown in fermentation vessels. In addition to carbon and nitrogen, phosphate, sulfate, iron, phosphorous, sodium, sulfur, potassium, magnesium, and trace elements are supplemented to the synthetic algal culture medium. In cases where more complex chemical additives are used such as corn steep liquor and yeast extract, trace elements and vitamins can be omitted as these additives contain adequate quantities of these nutrients.

Generally, previously described recipes for heterotrophic culture media used to cultivate microalgae always contain chemical additives. Trace elements are also derived from chemical sources. Macro and micro nutrients are often chemically derived. Corn steep liquor is an industrial byproduct derived from the wet-milling of corn, to which a chemical, sulfur dioxide gas, is often injected into the steep to facilitate the softening of corn kernel. Nitrogen sources such as ammonium, nitrate, MSG are all products of industrial processes where chemicals are required to synthesize or isolate the product. Non-organic yeast extract is produced using culture medium that contains nutrients derived from chemicals. Other compounds that have been proposed for industrial production of Thaurstochydrids are gelysate, peptone, tryptone, casein, urea, whey, or corn gluten meal, all products of industrial processes where chemicals are required to synthesize or isolate the product. Such media is unsuitable for the production of algae and algae-derived compositions and compounds that are chemical free or certified organic.

The US National Organic Program establishes rules regarding organic practices and labeling. Substances that are allowed and not allowed are outlined and added to the National List. The List includes synthetically-derived substances such as DHA and EPA. Substances that are not allowed under the NOP guidelines are non-organic yeast and products derived from non-organic yeast, synthetically-derived sulfate, and synthetically-derived trace elements, to name a few. Up to 5% of a non-organic substance has been allowed under current law given 1) the USDA establishes they provide a health benefit and 2) an organic alternative is not available. Organic products that contain the synthetically-derived DHA have been allowed to be marketed and sold. The algal DHA industry has maintained that a process for the organic production of algal DHA cannot be developed. As a result, the addition of non-organic algal oil to organic labelled baby formula and other foods remains controversial.

Accordingly, there is a need for the commercial scale production of algae and their constituent components that are free of chemical additives and preservatives, including those that are certified organic, for use in food, pharmaceutical and cosmetic and industrial products.

SUMMARY

Methods are provided for producing algal cultures, biomass, lipid compounds and lipid compositions, and related products.

In one illustrative embodiment, a method is provided for producing an algal biomass or algal cell culture, comprising growing algae in a culture medium and harvesting the algal biomass or algal cell culture from the medium, wherein the medium comprises juice from one or more fruits, a source of oxygen, and nitrogen, wherein the medium is sterilized, and wherein the nitrogen in the medium consists of natural nitrogen.

In another illustrative embodiment, the medium can be supplemented with a source of salt. In another illustrative embodiment, the source of salt can be sea water. In a further embodiment, the sea water can have a salinity in the range of about 10 ppt to about 35 ppt.

In further illustrative embodiments, the medium of any of the above mentioned embodiments can be supplemented with a sugar. In another embodiment, the sugar can be dextrose or fructose. In another embodiment, the sugar can be certified organic.

In another illustrative embodiment, the medium can consist of the juice, the source of oxygen, the nitrogen, a sugar and a source of salt. In another illustrative embodiment, the medium can consist of the juice, the source of oxygen, the nitrogen and a sugar. In yet another illustrative embodiment, the medium can consist of the juice, the source of oxygen, the nitrogen and a source of salt.

In another illustrative embodiment, a method is provided for producing an algal biomass or algal cell culture, comprising growing algae in a culture medium and harvesting the algal biomass or algal cell culture from the medium, wherein the medium consists of juice from one or more fruits or vegetables or any combination of fruits and vegetables, a sugar, a source of salt, a source of oxygen, and nitrogen, wherein the medium is sterilized, and wherein the nitrogen in the medium consists of natural nitrogen.

In another illustrative embodiment, a method is provided for producing an algal biomass or algal cell culture, comprising growing algae in a culture medium and harvesting the algal biomass or algal cell culture from the medium, wherein the medium consists of juice from one or more fruits or vegetables or any combination of fruits and vegetables, a sugar, a source of oxygen, and nitrogen, wherein the medium is sterilized, and wherein the nitrogen in the medium consists of natural nitrogen.

In another illustrative embodiment, a method is provided for producing an algal biomass or algal cell culture, comprising growing algae in a culture medium and harvesting the algal biomass or algal cell culture from the medium, wherein the medium consists of juice from one or more fruits or vegetables or any combination of fruits and vegetables, a source of salt, a source of oxygen, and nitrogen, wherein the medium is sterilized, and wherein the nitrogen in the medium consists of natural nitrogen.

In further illustrative embodiments, the sugar of any of the embodiments of the preceding four paragraphs can be dextrose or fructose. In a further illustrative embodiment, the sugar can be certified organic. In another illustrative embodiment, the source of salt of any of the embodiments of the preceding four paragraphs can be sea water. In a further embodiment, the sea water can have a salinity of in the range of about 10 ppt to about 35 ppt.

In another illustrative embodiment, there is provided a method of producing one or more lipid compounds or compositions thereof, comprising growing algae in a medium and extracting the compound or composition from the algae, wherein the medium comprises juice from one or more fruits or vegetables or from any combination of fruits and vegetables, a source of oxygen, and nitrogen, wherein the medium is sterilized and wherein the nitrogen in the medium consists of natural nitrogen.

In another illustrative embodiment, the medium of the embodiment of the preceding paragraph can be supplemented with a source of salt. In another illustrative embodiment, the source of salt can be sea water. In a further embodiment, the sea water can have a salinity in the range of about 10 ppt to about 35 ppt.

In further illustrative embodiments, the medium of any of the embodiments of the two preceding paragraphs can be supplemented with a sugar. In another embodiment, the sugar can be dextrose or fructose. In another embodiment, the sugar can be certified organic.

In another illustrative embodiment, the medium can consist of the juice, the source of oxygen, the nitrogen, a sugar and a sterilized source of salt. In yet another illustrative embodiment, the medium can consist of the juice, the source of oxygen, the nitrogen and a sugar. In another illustrative embodiment, the medium can consist of the juice, the source of oxygen, the nitrogen and a source of salt.

In another illustrative embodiment, there is provided a method of producing one or more lipid compounds or compositions thereof, comprising growing algae in a medium and extracting the compound or composition from the algae, wherein the medium consists of juice from one or more fruits or vegetables or from any combination of fruits and vegetables, a source of oxygen, nitrogen, a source of salt, and a sugar, wherein the medium is sterilized and wherein the nitrogen in the medium consists of natural nitrogen.

In another illustrative embodiment, there is provided a method of producing one or more lipid compounds or compositions thereof, comprising growing algae in a medium and extracting the compound or composition from the algae, wherein the medium consists of juice from one or more fruits or vegetables or from any combination of fruits and vegetables, a source of oxygen, nitrogen, and a source of salt, wherein the medium is sterilized and wherein the nitrogen in the medium consists of natural nitrogen.

In another illustrative embodiment, there is provided a method of producing one or more lipid compounds or compositions thereof, comprising growing algae in a medium and extracting the compound or composition from the algae, wherein the medium consists of juice from one or more fruits or vegetables or from any combination of fruits and vegetables, a source of oxygen, nitrogen, and a sugar, wherein the medium is sterilized and wherein the nitrogen in the medium consists of natural nitrogen.

In further illustrative embodiments, the sugar of any of the embodiments of the preceding four paragraphs can be dextrose or fructose. In a further illustrative embodiment, the sugar can be certified organic. In another illustrative embodiment, the source of salt of any of the embodiments of the preceding four paragraphs can be sea water. In a further embodiment, the sea water can have a salinity in the range of about 10 ppt to about 35 ppt.

In various illustrative embodiments, the compound of any of the above embodiments can be a fatty acid, a carotenoid or a fat-soluble vitamin. In a further illustrative embodiment, the fatty acid can be a polyunsaturated fatty acid. In a further illustrative embodiment, the polyunsaturated fatty acid can be selected from the group consisting of DHA, EPA, DPA, and pinolenic acid. In a further illustrative embodiment, the polyunsaturated fatty acid can be DHA. In a further illustrative embodiment, the polyunsaturated fatty acid can be EPA. In a further illustrative embodiment, the polyunsaturated fatty acid can be pinolenic acid. In a further illustrative embodiment, the polyunsaturated fatty acid can be DPA. In a further illustrative embodiment, the carotenoid can be beta-carotene.

In a further illustrative embodiment, there is provided a method of producing a food product, cosmetic, industrial composition or pharmaceutical composition for a human or an animal, comprising the steps of: growing algae in a culture medium and harvesting an algal biomass or algal cell culture from the medium, wherein the medium comprises juice from one or more fruits or vegetables or any combination of fruits and vegetables, a source of oxygen, and nitrogen, wherein the medium is sterilized, and wherein the nitrogen in the medium consists of natural nitrogen; harvesting an algal biomass or algal cell culture from the medium; and preparing the food product, industrial composition or pharmaceutical composition.

In a further illustrative embodiment, the method of the preceding paragraph can further comprise extracting one or more lipid compounds or compositions thereof from the algal biomass or algal cell culture and preparing the food product, industrial composition of pharmaceutical composition. In a further illustrative embodiment, the lipid compound can be a fatty acid, carotenoid or fat soluble vitamin. In a further embodiment, the fatty acid can be a polyunsaturated fatty acid. In a further embodiment, the polyunsaturated fatty acid can be selected from the group consisting of DHA, DPA, EPA and pinolenic acid. In a further illustrative embodiment, the polyunsaturated fatty acid can be DHA. In a further illustrative embodiment, the polyunsaturated fatty acid can be EPA. In a further illustrative embodiment, the polyunsaturated fatty acid can be pinolenic acid. In a further illustrative embodiment, the carotenoid can be beta-carotene.

In further illustrative embodiments, the medium of any of the embodiments of the above two preceding paragraphs can be supplemented with a source of salt. In a further embodiment, the source of salt can be sea water. In a further embodiment, the sea water can have a salinity of in the range of about 10 ppt to about 35 ppt.

In further illustrative embodiments, the medium of any of the embodiments of the above three preceding paragraphs can be supplemented with a sugar. In a further embodiment, the sugar can be dextrose or fructose. In a further embodiment, the sugar can be certified organic. In a further embodiment, the medium can be supplemented with dextrose and certified organic yeast extract.

In further illustrative embodiments, the preparation of any of the embodiments of the above four preceding paragraphs is that of a food product. In a further illustrative embodiment, the food product is a nutritional supplement.

In various illustrative embodiments, the algae of any of the above embodiments can belong to a genus selected from the group consisting of *Thraustochytrium*, *Chlamydomonas*, *Nannochloropsis*, *Nitzchia* and *Aurantiochytrium* (formerly *Schizochytrium*). In a further illustrative embodiment, the genus can be *Aurantiochytrium*. In a further illustrative embodiment, the genus can be *Nannochloropsis*. In a further illustrative embodiment, the genus can be *Chlamydomonas*. In a further illustrative embodiment, the genus can be *Nitzschia*.

In various illustrative embodiments, the growth of the algae of any of the above embodiments can be heterotrophic or mixotrophic.

In various illustrative embodiments, the juice any of the above embodiments can be selected from the group consisting of tomato juice, beet juice, carrot juice, coconut juice and apple juice. In a further illustrative embodiment, the juice can be beet juice. In a further illustrative embodiment, the juice can be tomato juice. In a further illustrative embodiment, the juice can be carrot juice. In a further illustrative embodiment, the juice of any of the embodiments is hydrolyzed with non-GMO invertase. In a further illustrative embodiment, the juice of any of the embodiments herein is beet juice and the juice is hydrolyzed with non-GMO invertase.

In various illustrative embodiments, the juice of any of the above embodiments can have a percent concentration in the medium of about 5% to about 70%. In a further illustrative embodiment, the juice can have a percent concentration in the medium of about 10% to about 50%. In a further illustrative embodiment, the juice can have a percent concentration in the medium selected from the group consisting of about 10%, about 25% and about 50%.

In further illustrative embodiments, the juice of any of the above embodiments can be fermented.

In further illustrative embodiments, the juice of any of the above embodiments can be pasteurized.

In further illustrative embodiments, the juice of any of the above embodiments can be certified organic.

In further illustrative embodiments, the medium of any of the above embodiments can have a pH in the range of about 3 to about 9.

In further illustrative embodiments, the medium of any of the above embodiments can be free of chemical additives and preservatives.

In further illustrative embodiments, the medium of any of the above embodiments can be supplemented with certified organic yeast extract.

In further illustrative embodiments, the algal biomass, algal cell culture, lipid compound or composition, food product or nutritional supplement of any of the above mentioned embodiments can be certified organic.

DETAILED DESCRIPTION OF THE INVENTION

Figure 1A:
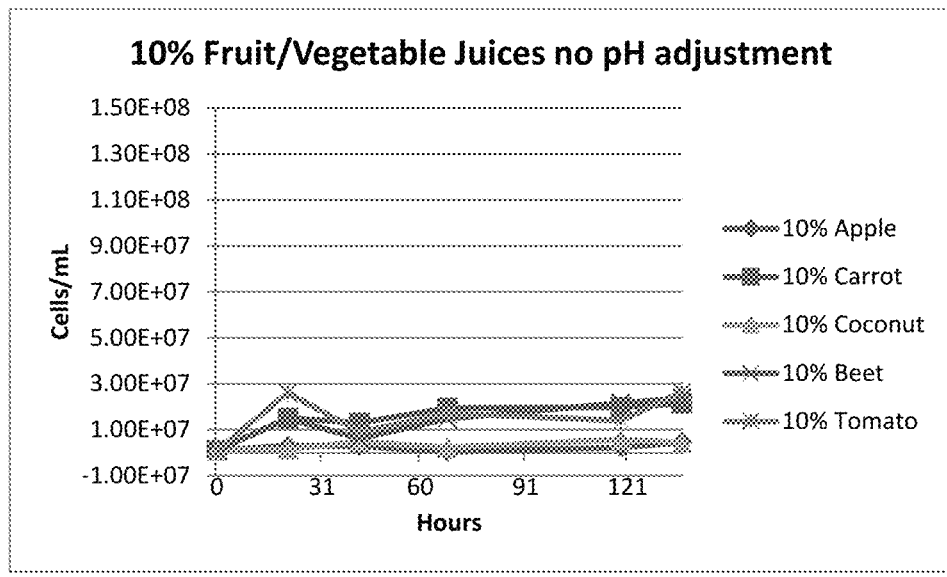
FIGS. 1A-1C are line graphs showing the growth of *A. limacinum* (*Aurantiochytrium limacinumin*) juice media and seawater with no pH adjustment.

The inventors have discovered a cost effective means to produce algae naturally using a fruit and/or vegetable juice-derived medium as a nitrogen source and as a source of micronutrients, macronutrients and vitamins. This medium, when pasteurized or otherwise sterilized to preserve nutrient quality and to reduce natural bio-burden, offers a complete and suitable medium for algae growth and contains natural nitrogen and natural growth factors that can be used to obtain high algal biomass. In one embodiment, the medium can be supplemented with a carbon source such as fructose, ethanol, glycerin or dextrose to boost the production of desirable products such as omega-3 fatty acids and other lipid compounds and compositions. In another embodiment, the medium of any of the embodiments herein can be supplemented with dextrose. In another embodiment, the juice and carbon supplements selected can be certified organic and produced free of chemical additives and preservatives so that the resulting algal biomass, algal cell culture and/or lipid extracts from the algae and related products can also be certified organic. In another embodiment, the medium of any of the embodiments herein can be supplemented with dextrose and certified organic yeast extract. In another embodiment, the medium of any of the embodiments herein can be supplemented with certified organic yeast extract. In another embodiment, different types of fruit and/or vegetable juices type can be combined to obtain an optimal formulation for producing lipid extracts of interest such as omega-3 fatty acids or carotenoids. In another embodiment, the juice can be fermented to release key nutrients and to adjust pH values to improve growth. In some embodiments, the juice selection can enhance the fatty acid profile and the percentage DHA of total oils of the algae. In some embodiments, the natural antioxidants in the juices can improve fatty acid stability and reduce the rate of oxidation of fatty acids. For example, the beta-carotene in carrot juice can be extracted directly into the oil. The beta-carotene can act as a natural stabilizer for the oil. In one embodiment, the juice of any of the embodiments herein improves the stability of fatty acids, the fatty acids can be DHA, and the juice can be beet juice, carrot juice or blueberry juice. In another embodiment, the juice of any of the embodiments herein reduces the rate of oxidation of fatty acids, the fatty acids can be DHA, and the juice can be beet juice, carrot juice or blueberry juice.

Methods are provided herein for producing algal cultures and biomass and lipid compounds and compositions, as well as related products.

In one illustrative embodiment, there is provided a method of producing an algal biomass or algal cell culture, comprising growing algae in a culture medium and harvesting the algal biomass or algal cell culture from the medium, wherein the medium comprises juice from one or more fruits or vegetables or any combination of fruits and vegetables, a source of oxygen, and nitrogen, wherein the medium is sterilized, and wherein the nitrogen in the medium consists of natural nitrogen.

In another illustrative embodiment, there is provided a method of reducing the rate of oxidation of a lipid compound or composition, comprising suspending the lipid compound or composition in a medium, wherein the medium comprises juice from one or more fruits or vegetables or from any combination of fruits and vegetables. In a further illustrative embodiment, the medium is pasteurized or sterilized. In a further illustrative embodiment, the juice is selected from the group consisting of beet juice, carrot juice, and blueberry juice. In a further embodiment, the juice is beet juice. In a further embodiment, the lipid compound is DHA. In a further embodiment, the juice is certified organic. In a further illustrative embodiment, the lipid compound or composition is produced by any of the methods illustrated herein. In a further illustrative embodiment, the lipid compound or composition is derived from algae.

As used herein, "algal biomass" includes algal cells and cell fragments and their constituent components.

As defined herein, a "source of oxygen" refers to any source of oxygen capable of being assimilated by algae. In various illustrative embodiments, the source of oxygen of any of the embodiments herein can be selected from the group consisting of filtered air, oxygenation by agitation or a filtered oxygen stream.

As defined herein, "natural nitrogen" is one or more of: (i) any nitrogen or source of nitrogen that naturally occurs in juice; and (ii) any nitrogen or source of nitrogen that is used to supplement algal media in order to provide nitrogen to the algae and that is certified organic and/or is free of chemical additives and preservatives. Natural nitrogen is distinguished from any source of nitrogen that is not certified organic or that is a chemical additive or preservative, such as non-organic yeast extract, ammonium chloride, casitone, peptone, tryptone, polypeptone, corn steep liquor, corn steep solids, ammonium acetate, and sodium nitrate.

In various illustrative embodiments, the natural nitrogen of any embodiment herein can be nitrogen and compounds containing nitrogen, all of which naturally occur in juice. In further illustrative embodiments, the natural nitrogen of any embodiments herein can be nitrogen and compounds containing nitrogen, all of which naturally occur in juice, as well as any algal media nitrogen supplement that is certified organic. In another illustrative embodiment, the natural nitrogen is certified organic yeast extract.

In various illustrative embodiments, the algae of any of the embodiments herein are grown to such amounts and/or density biomass as are sufficient for commercial or industrial scale production.

In various illustrative embodiments, the medium described herein can be supplemented with a source of salt.

As used herein, a "source of salt" refers to any salt, or combinations thereof, that is capable of being metabolized by algae.

In various illustrative embodiments, the source of salt of any of the embodiments herein can be selected from the group consisting of artificial sea salt, natural sea water or natural sea salt. In various illustrative embodiments, the source of salt can be sea water. In a further illustrative embodiment, the sea water can have a salinity in the range of about 0.5 ppt to about 35 ppt, about 0.5 to about 25 ppt, about 0.5 to about 20 ppt, about 0.5 to about 15 ppt, about 5 to about 15 ppt, about 5 to about 20 ppt, about 5 to about 25 ppt, about 10 to about 20 ppt, and about 5 to about 35 ppt. In a further illustrative embodiment, the sea water can have a salinity selected from the group consisting of about 0.5 ppt, about 1.0 ppt, about 2.0 ppt, about 3.0 ppt, about 4.0 ppt, about 5.0 ppt, about 7.0 ppt, about 10 ppt, about 12 ppt, about 15 ppt, about 20 ppt, about 25 ppt, about 30 ppt, and about 35 ppt. In a further embodiment, the sea water can have a salinity of about 10 ppt, 10.7 ppt, 12 ppt, 12.7 ppt, 15 ppt, or 15.7 ppt.

In various illustrative embodiments, the medium described herein can be supplemented with a sugar.

As used herein, a "sugar" refers to any one or more carbohydrates, whether simple or complex, that is a source of nutrition for algae. A "sugar" also includes dextrose, ethanol and certified organic vegetable glycerin.

In various illustrative embodiments, the sugar of any of the embodiments herein can be ethanol, fructose, glucose, sucrose or dextrose, or any combination thereof. In a further illustrative embodiment, the sugar can be certified organic. In another embodiment, the sugar can be present in the medium at a concentration of about 1% to about 20%, about 1% to about 10%, about 2% to about 10%, about 2% to about 8%, or about 5% to about 10%. In another embodiment, the sugar can be present in the medium at a concentration of about 1%, about 2%, about 3%, about 4%, about 5%, about 6%, about 7%, about 8%, about 9%, about 10%, about 12%, about 15%.

In various illustrative embodiments, the medium described herein can consist of the juice, the source of oxygen, the nitrogen, a sugar and a source of salt. In various illustrative embodiments, the medium described herein can consist of the juice, the source of oxygen, the nitrogen and a sugar. In various illustrative embodiments, the medium described herein can consist of the juice, the source of oxygen, the nitrogen and a source of salt.

In another illustrative embodiment, there is provided a method of producing one or more lipid compounds or compositions thereof, comprising growing algae in a medium and extracting the compound or composition from the algae, wherein the medium comprises juice from one or more fruits or vegetables or any combination of fruits and vegetables, a source of oxygen, and nitrogen, wherein the medium is sterilized, and wherein nitrogen in the medium consists of natural nitrogen.

As used herein, a "lipid compound" refers to any fat, oil, lipid or other compound that dissolves in fats, oils, lipids and non-polar solvents such as hexane or toluene. In various illustrative embodiments, the lipid compound of any of the embodiments herein can be a fatty acid, a carotenoid or a fat-soluble vitamin.

As used herein, a "fatty acid" refers to a molecule comprised of a carboxylic acid residue linked to a carbon chain. This carbon chain can range from short (6 carbons) to very long (greater than 20 carbons) and can be either saturated or unsaturated. In various illustrative embodiments, the lipid compound of any of the embodiments herein can be a fatty acid. In another illustrative embodiment, the fatty acid can be coniferic acid. In another illustrative embodiment, the fatty acid can be an unsaturated or polyunsaturated fatty acid. In another illustrative embodiment, the unsaturated fatty acid can be an omega fatty acid. In another illustrative embodiment, the omega fatty acid can be selected from the group consisting of omega-3 fatty acid, omega-6 fatty acid, omega-7 fatty acid and omega-9 fatty acid. In another illustrative embodiment, the omega fatty acid can be an omega-3 fatty acid. In another illustrative embodiment, the omega fatty acid can be an omega-7 fatty acid. In another illustrative embodiment, the fatty acid can be a polyunsaturated fatty acid. In another illustrative embodiment, the polyunsaturated fatty acid can be selected from the group consisting of Docosahexaenoic acid (DHA), Eicosapentaenoic acid (EPA), Docosapentaenoic acid (DPA), and pinolenic acid. In a further illustrative embodiment, the polyunsatured fatty acid can be DHA. In a further illustrative embodiment, the polyunsaturated fatty acid can be EPA. In a further illustrative embodiment, the polyunsaturated fatty acid can be pinolenic acid. In a further illustrative embodiment, the polyunsaturated fatty acid can be DPA.

As used herein, a "carotenoid" refers to fat-soluble pigments of the tetraterpenoid family. In various illustrative embodiments, the carotenoid of any of the embodiments herein can be a carotenoid selected from the group consisting of beta-carotene, astaxanthin and lycopene. In a further illustrative embodiment, the carotenoid can be astaxanthin. In a further illustrative embodiment, the carotenoid can be beta-carotene. In a further illustrative embodiment, the carotenoid can be lycopene. In a further illustrative embodiment, the carotenoid can have antioxidant activity.

As used herein, a "fat-soluble vitamin" refers to a vitamin, namely a substance that is essential in small doses for normal metabolism in the body, that is dispersed in and stored in fat. In various illustrative embodiments, the fat soluble vitamin of any of the embodiments herein can be a vitamin selected from the group consisting of retinal (Vitamin A), ergocalciferol (Vitamin D2), cholecalciferol (Vitamin D3), alpha-tocopherol (Vitamin E) phylloquinone (vitamin K) and Ubiquinol (Coenzyme Q). In a further illustrative embodiment, the fat soluble vitamin can be Vitamin A. In a further illustrative embodiment, the fat soluble vitamin can be Vitamin E.

In a further illustrative embodiment, there is provided a method of producing a food product, cosmetic, industrial composition or pharmaceutical composition for a human or an animal, comprising the steps of: growing algae in a culture medium and harvesting an algal biomass or algal cell culture from the medium, wherein the medium comprises juice from one or more fruits or vegetables or any combination of fruits and vegetables, a source of oxygen, and nitrogen, wherein the medium is sterilized, and wherein nitrogen in the medium consists of natural nitrogen; harvesting an algal biomass or algal cell culture from the medium; and preparing the food product, cosmetic, industrial composition or pharmaceutical composition.

In a further illustrative embodiment, the method can further comprise extracting one or more lipid compounds or compositions thereof from the algal biomass or algal cell culture and preparing the food product, cosmetic, industrial composition or pharmaceutical composition.

In a further illustrative embodiment, the method can further comprise preparing a food product. As used herein, a "food product" refers to any food for animal or human consumption, and includes both solid and liquid compositions. A food product can be an additive to animal or human foods. Food products include, but are not limited to, common foods; liquid products, including milks, beverages, therapeutic drinks, powdered drinks and nutritional drinks; functional foods; nutritional supplements; nutraceuticals; infant formulas, including formulas for pre-mature infants; food for infants; foods for pregnant or nursing women; foods for adults; geriatric foods; and animal foods.

In further illustrative embodiments, the food product of any of the embodiments herein is a nutritional supplement. As defined herein, a "nutritional supplement" is any preparation (whether in capsule, gel, liquid or powder form) intended to supplement the diet and provide nutrients, such as vitamins, minerals, fiber, fatty acids, or amino acids that may be missing or may not be consumed in sufficient quantities in a person's diet. Non-limiting examples of a nutritional supplement include vitamin supplements, polyunsaturated fatty acid supplements, omega-3 fatty acid supplements, omega-7 fatty acids, supplements containing DHA and/or EPA, and nutritional supplements containing algae or algal derivatives.

In one illustrative example, the nutritional supplement contains one or more fat-soluble vitamins. In another illustrative example, the nutritional supplement contains algal cells or algal biomass. In another illustrative example, the nutritional supplement contains omega-3 fatty acids. In another illustrative example, the nutritional supplement contains omega-7 fatty acids. In another illustrative example, the nutritional supplement contains polyunsaturated fatty acids. In another illustrative example, the nutritional supplement contains polyunsaturated fatty acids selected from the group consisting of DHA, DPA, EPA, and pinolenic acid. In another illustrative example, the nutritional supplement contains DHA and EPA. In another illustrative example, the nutritional supplement contains DHA. In another illustrative example, the nutritional supplement contains EPA. In various illustrative examples, the nutritional supplement of any of the embodiments herein can be certified organic. In another illustrative example, the nutritional supplement contains antioxidants.

An "animal" means any non-human organism belonging to the kingdom Animalia, and includes, without limitation, aquatic animals and terrestrial animals. The term "animal feed" or "animal food" refers to any food intended for non-human animals, whether for fish; commercial fish; ornamental fish; fish larvae; bivalves; mollusks; crustaceans; shellfish; shrimp; larval shrimp; artemia; rotifers; brine shrimp; filter feeders; amphibians; reptiles; mammals; domestic animals; farm animals; zoo animals; sport animals; breeding stock; racing animals; show animals; heirloom animals; rare or endangered animals; companion animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; rodents such as mice, rats, hamsters and guinea pigs; and so on. An animal feed includes, but is not limited to, an aquaculture feed, a domestic animal feed including pet feed, a zoological animal feed, a work animal feed, a livestock feed, or a combination thereof.

In some illustrative embodiments, the food product is a medical food. As used herein, a "medical food" is a food that is in a composition to be consumed or administered externally under the supervision of a physician and that is intended for the specific dietary management of a condition, for which distinctive nutritional requirements, based on recognized scientific principles, are established by medical evaluation.

As defined herein, a "cosmetic" includes, but is not limited to, emulsions, creams, lotions, masks, soaps, shampoos, washes, facial creams, conditioners, make-ups, bath agents, and dispersion liquids. Cosmetic agents can be medicinal or non-medicinal.

As defined herein, a "pharmaceutical composition" includes, but is not limited to, an anti-inflammatory composition, a drug for treatment of coronary heart disease, a drug for treatment of arteriosclerosis, a chemotherapeutic agent, an active excipient, an osteoporosis drug, an antidepressant, an anticonvulsant, an anti-*Helicobacter pylori* drug, a drug for treatment of neurodegenerative disease, a drug for treatment of degenerative liver disease, an antibiotic, a cholesterol lowering composition, and a triglyceride lowering composition.

In further illustrative embodiments, the algae of any of the embodiments herein that can be used include *Chlorophyta* such as *Charoides* (e.g., *Charoides, Lamprothamnium, Nitellopsis*, and *Nitella*), *Zynematales* (e.g., *Zygnema, Closterium*, and *Netrium*), *Codials* (e.g., *Codium fragile, Helimida opunta*, and *Caulerpa*), *Bryopsis plumosa* (e.g., *Bryopsis, Pseudobryopsis, Bryopsidella, Derbesis*, and *Pedobesia*), *Acetabularia Ryukyuensis* (e.g., *Acetabularia Ryukyuensis, Halicoryne wrightii, Neomeris annulata, Cymopolia van bossei, Bornettella ovalis*, and *Acetabularia calyculus*), *Siphonocladales* (e.g., Valoniaceae and Boodleaceae), *Cladophora* (e.g., *Anadyomene writii, Cladophora, Cladophora sauteri*, and *Chaetomorpha*), *Ulva* (e.g., *Ulva* and *Fnteromorpha*), *Ulotrichales* (e.g., Acrosiphoniaceae, Collinsiellaceae, Monostromaceae, and Chlorocystidaceae), *Prasiola, Chlorella, Chlorococcales* (e.g., *Pediastrum* and *Hydrodictyon*), *Aurantiochytrium* (e.g., *Aurantiochytrium limacinum*), *Nannochloropsis* (e.g., *Nannochloropsis oculata*), *Nitzchia, Chlamydomonas* (e.g., *Chlamydomonas reinhardtii*), and *Volvocales* (e.g., *Chlamydomonus, Pandorina, Pleodorina*, and Volvox).

In a further illustrative embodiment, the algae can belong to a genus selected from the group consisting of *Thraustochytrium, Chlamydomonas, Nitzchia, Nannochloropsis* and *Aurantiochytrium*. In a further illustrative embodiment, the genus can be *Aurantiochytrium*. In a further illustrative embodiment, the genus can be *Nannochloropsis*. In a further illustrative embodiment, the genus can be *Chlamydomonas*. In a further illustrative embodiment, the genus can be *Nitzschia*.

In a further illustrative embodiment, the algae of any of the embodiments herein is not a genetically modified organism (i.e., a non-genetically modified organism or non-GMO) or a transgenic organism, or is otherwise free of genetic material that has been altered using genetic engineering.

In various illustrative embodiments, the growth of the algae of any of the embodiments herein can be heterotrophic or mixotrophic.

In various illustrative embodiments, the medium of any of the embodiments herein can be used to both inoculate and culture the algae. In one illustrative embodiment, the algal cells are first inoculated in a medium of any of the embodiments therein, and subsequently the inoculum is transferred to a higher volume of the same medium, such that the inoculum makes up a certain percentage (e.g. 10%) of the total volume of the final culture medium.

As used herein, "juice" refers to the aqueous liquid expressed or extracted from one or more fruits or vegetables or any combination of fruits and vegetables, purees of the edible portions of one or more fruits or vegetables any combination of fruits and vegetables, or any concentrates of such liquid or puree. As used herein, the term "juice" also includes beet molasses. In various illustrative embodiments, the juice of any of the embodiments herein contains all of the compounds (including sugars, nitrogen and other naturally occurring vitamins, minerals and macronutrients) that naturally occur in the juice and such juice has not been processed or modified so as to remove any such compounds.

In various illustrative embodiments, the juice any of the embodiments herein can be a juice from one or more fruits or vegetables, or any combination of fruits and vegetables, selected from the group consisting of acerolas, apples, apricots, bananas, blackberries, blueberries, boysenberries, cantaloupes, cherries, coconut, crabapples, cranberries, currants, dates, dewberries, elderberries, figs, gooseberries, grapes, grapefruits, guanabanas, guavas, kiwis, lemons, limes, loganberries, melons, mangos, nectarines, oranges, papayas, passion fruit, peaches, pears, pineapples, plums, pomegranates, prunes, quince, raspberries, rhubarb, strawberries, tangerines, tomatoes, watermelons, beets, bell peppers, broccoli, cabbages, carrots, celery, cucumbers, fennel, kale, parsnips, pumpkins, radicchio, sweet potato, radish, tomatillo, turnip, yam, and zucchini.

In a further illustrative embodiment, the juice can be a juice selected from the group consisting of tomato juice, beet juice, carrot juice, coconut juice and apple juice. In a further illustrative embodiment, the juice can be a juice selected from the group consisting of tomato juice, beet juice, carrot juice, and apple juice. In a further illustrative embodiment, the juice can be a juice selected from the group consisting of tomato juice, beet juice, and carrot juice. In another illustrative embodiment, the juice can be beet juice. In a further illustrative embodiment, the juice can be tomato juice. In a further illustrative embodiment, the juice can be carrot juice.

In further illustrative embodiments, the juice of any of the embodiments herein can be hydrolyzed with one or more enzymes capable of breaking down sugars in the juice. In one illustrative embodiment, the enzyme is non-GMO invertase. In another illustrative embodiment, the juice that is hydrolyzed with non-GMO invertase is beet juice.

In various illustrative embodiments, the total amount of bioavailable nitrogen in the juice can be greater or equal to 20 mg nitrogen/L. In various illustrative embodiments, the total amount of bioavailable nitrogen in the juice can be greater or equal to 40 mg nitrogen/L. In various illustrative embodiments, the total amount of bioavailable nitrogen in the juice can be greater or equal to 100 mg nitrogen/L. In various illustrative embodiments, the total amount of bioavailable nitrogen in the juice can be greater or equal to 200 mg nitrogen/L. In various illustrative embodiments, the total amount of bioavailable nitrogen in the juice can be greater or equal to 300 mg nitrogen/L. In various further illustrative embodiments, the total amount of bioavailable nitrogen in the juice can be greater or equal to 334 mg nitrogen/L. In various further illustrative embodiments, the total amount of bioavailable nitrogen in the juice can be greater or equal to 350 mg nitrogen/L. In various further embodiments, the total amount of bioavailable nitrogen in the juice can be greater or equal to 400 mg nitrogen/L. In various further embodiments, the total amount of bioavailable nitrogen in the juice can be greater or equal to 550 mg nitrogen/L. In various illustrative embodiments, the total amount of bioavailable nitrogen in the juice can be greater or equal to 600 mg nitrogen/L. In various illustrative embodiments, the total amount of bioavailable nitrogen in the juice can be greater or equal to 700 mg nitrogen/L. In various further illustrative embodiments, the total amount of bioavailable nitrogen in the juice can be greater or equal to 732 mg nitrogen/L. In various illustrative embodiments, the total amount of bioavailable nitrogen in the juice can be greater or equal to 800 mg nitrogen/L.

In various further embodiments, the total amount of bioavailable nitrogen in the juice can be in the range of about 10 mg nitrogen/L to about 1700 mg nitrogen/L. In a further embodiment, the total amount of bioavailable nitrogen in the juice can be in the range of about 20 mg nitrogen/L to about 900 mg nitrogen/L. In a further embodiment, the total amount of bioavailable nitrogen in the juice can be in the range of about 30 mg nitrogen/L to about 850 mg nitrogen/L. In a further embodiment, the total amount of bioavailable nitrogen in the juice can be in the range of about 35 mg nitrogen/L to about 820 mg nitrogen/L.

In a further embodiment, the total amount of bioavailable nitrogen in the juice can be selected from the group consisting of about: 10 mg nitrogen/L, 20 mg nitrogen/L, 30 mg nitrogen/L, 40 mg nitrogen/L, 50 mg nitrogen/L, 80 mg nitrogen/L, 90 mg nitrogen/L, 100 mg nitrogen/L, 110 mg nitrogen/L, 118 mg nitrogen/L, 120 mg nitrogen/L, 130 mg nitrogen/L, 140 mg nitrogen/L, 150 mg nitrogen/L, 200 mg nitrogen/L, 250 mg nitrogen/L, 300 mg nitrogen/L, 310 mg nitrogen/L, 320 mg nitrogen/L, 330 mg nitrogen/L, 334 mg nitrogen/L, 340 mg nitrogen/L, 350 mg nitrogen/L, 400 mg nitrogen/L, 450 mg nitrogen/L, 500 mg nitrogen/L, 550 mg nitrogen/L, 600 mg nitrogen/L, 650 mg nitrogen/L, 700 mg nitrogen/L, 710 mg nitrogen/L, 720 mg nitrogen/L, 730 mg nitrogen/L, 732 mg nitrogen/L, 740 mg nitrogen/L, 750 mg nitrogen/L, 800 mg nitrogen/L, 810 mg nitrogen/L, 813 mg nitrogen/L, 820 mg nitrogen/L, 830 mg nitrogen/L, 850 mg nitrogen/L, 900 mg nitrogen/L, 950 mg nitrogen/L, 1000 mg nitrogen/L, 1500 mg nitrogen/L and 1700 mg nitrogen/L.

In various illustrative embodiments, the juice of any of the embodiments herein can have a percent concentration in the medium which percent concentration is in the range of about 5% to about 100%. In a further illustrative embodiment, the percentage concentration of the juice in the medium can be a percent concentration selected from the group consisting of about: 5%, 10%, 15%, 20%, 25%, 30%, 35%, 40%, 45%, 50%, 55%, 60%, 65%, 70%, 80%, 90% and 100%. In a further illustrative embodiment, the percentage concentration of the juice in the medium can be a percent concentration in the range of about 5% to about 70%. In a further illustrative embodiment, the percentage concentration of the juice in the medium can be a percent concentration in the range of about 10% to about 50%. In a further illustrative embodiment, the percentage concentration of the juice in the medium can be a percent concentration selected from the group consisting of 10%, 25% and 50%.

In various illustrative embodiments, the juice of any of the embodiments herein can be fermented. In various illustrative embodiments, the juice of any of the embodiments herein can be sterilized by steam sterilization or pasteurization. In a further illustrative embodiment, the juice can be sterilized by pasteurization.

In further illustrative embodiments, the juice of any of the embodiments herein can be certified organic.

In further illustrative embodiments, the medium of any of the embodiments herein can have a pH selected from the group consisting of about 3, about 4, about 5, about 6, about 7, about 8, and about 9. In a further illustrative embodiment, the medium of any of the above embodiments can have a pH in the range of about 3 to about 8, about 3 to about 7, about 4 to about 7, about 5 to about 8, about 6 to about 7, or about 6 to about 8, or about 8 to about 9. In a further illustrative embodiment, the medium can have a pH of about 5.2, about 5.5, about 5.8, about 6.2, about 6.5, about 6.8, about 7.2, about 7.5, about 7.8, or about 8.0, or about 9.0.

In further illustrative embodiments, the medium of any of the embodiments herein can be free of chemical additives and preservatives.

As used herein, a "chemical additive or "chemical preservative" refers to any substance, other than a certified organic substance, that: (i) is not found in nature or that is a naturally occurring substance synthesized or extracted by chemical or industrial processes, and (ii) that is added, whether directly or indirectly, to an algal medium, culture or biomass, or to any component or constituent thereof in order to preserve, treat or enhance is in some way, or as a by-product of an industrial process. Non limiting examples of a chemical additive or preservative include ethylenediaminetetracetic acid (EDTA) and other chemical chelators, monosodium glutamate (MSG), corn steep liquor, corn steep solids, non-organic yeast extract, ammonium acetate, ammonium chloride, sodium nitrate, gelysate, peptone, tryptone, casitone, casein, urea, whey, corn gluten meal, synthetically derived sulfate and trace elements, sulfuric acid, hydrochloric acid, artificial sea water, and enzymes isolated using synthetic processes (non-limiting examples of which enzymes include alpha-amylase, fructofuranosidase and glucoamylase, and enzymes that have been isolated from genetically modified organisms).

As used herein, a "non-GMO" enzyme, such as for example non-GMO invertase, is an enzyme that has not been isolated from a genetically modified organism.

As used herein, a medium or other substance that is "free of chemical additives and preservatives" includes a medium or substance that has not been produced or processed using chemical additives and/or preservatives, or a medium or substance to which no chemical additives or preservatives have been added for its manufacture, growth, stabilization isolation or extraction. Such a medium may include, for example, non-GMO invertase or sugars that have been hydrolyzed with non-GMO invertase.

In further illustrative embodiments, the algal cell culture, algal biomass, lipid compounds or compositions of any of the embodiments herein can be certified organic.

As used herein, "certified organic" refers to the certification or labeling of a product or substance as organic by any government or government-approved body or entity having authority in its jurisdiction to issue such label or certification. Non-limiting examples are certifications issued under the authority of the US Department of Agriculture certifying that a product or substance is "organic", "95% organic"or "100% organic". As used herein, "non-organic" refers to any substance or product that is not certified organic.

The medium of the above mentioned embodiments can be prepared using techniques known in the art. Any juice, as that term is used herein, may be used to prepare the medium. Fruit and vegetable juices contain a variety of different sugars, vitamins, phytonutrients, pigments, phytohormones, amino acids and minerals. Fruit and vegetable juice therefore contain all the constitutive components normally found in synthetic algal culture medium.

In one exemplary embodiment, tomato juice is used. Tomato juice is suited for economical, large-scale production of algae and related compounds, compositions and products because it is relatively inexpensive. These characteristics of tomato juice make this juice an exemplary choice for the chemical-free cultivation of micro-algae. In another exemplary embodiment, certified organic tomato juice can be used to prepare the medium. The resulting algal biomass would meet NOP (organic) standards.

In another exemplary embodiment, naturally fermented beet juice may be used to prepare the medium.

The juice of any of the embodiments herein may be prepared by, for example, juicing one or more fruits or vegetables. The resulting juice is sterilized according to techniques well known in the art, which are described in Rupasinghe and Yu (2012), which is incorporated herein by reference in its entirety.

As defined herein, "sterilization", "sterilized" or "sterile" refers to a process which reduces or eliminates bio-burden to a level where it cannot compete with algae for growth. Non limiting examples include pasteurization, high hydrostatic pressure, steam sterilization and pulse electric field, and other techniques known in the art and described in Rupasinghe and Yu (2012).

In various exemplary embodiments, the juice of any of the embodiments herein can be pasteurized at a temperature selected from the group consisting of about 50 C, about 55 C, about 60 C, about 65 C, about 70 C, about 75 C, about 80 C, about 85 C, about 90 C, about 95 C and about 100 C.

In one exemplary embodiment, the pasteurized juice can be used directly in the media formulation. In another exemplary embodiment, the juice can be naturally pre-fermented using, for example, a lactic acid producing bacterium or a yeast, and then pasteurized to reduce bio-burden. The yeast or bacteria are added to the juice and sealed into vessels to initiate fermentation. Fermentation of the juice is tightly controlled to avoid undesirable or toxic by-products and spoilage. The quality of the final product is determined by the specific composition of the fruit used in the fermentation medium and the characteristics of the yeast or bacterial strain selected to ferment the juice. In one exemplary embodiment, fermentation is carried out in minimally processed juice with no other exogenously added growth factors, fertilizer, chemical reagents or nutrients. In another exemplary embodiment, the medium is supplemented with a sterilized sugar and/or sterilized source of salt to promote algal growth.

A source of oxygen is also added to the medium. In one exemplary embodiment, the medium can be mixed with ozonated fresh water or UV sterilized seawater. Ozonation and UV sterilization may be carried out according to techniques well known in the art, which are disclosed, for example in Kelley (1961) and Restaino et al. (1995), which is incorporated herein by reference in its entirety.

Sterilization of the medium may be achieved by techniques known in the art. In one illustrative embodiment, individual components of the medium, such as juice, sugar and a source of salt can first be sterilized individually according to one or more of the sterilization techniques known in the art and described in Rupasinghe and Yu (2012), and then combined under sterile conditions to produce a sterile medium. In another illustrative embodiment, individual non-sterilized components of the medium such as juice, sugar and a source of salt can first be combined and the resulting medium can then be sterilized in accordance with one or more of the techniques known in the art and described in Rupasinghe and Yu (2012).

This basal juice medium can then be used to culture algae. The algae may be cultured according to techniques well known in the art. In one exemplary embodiment, the algae are cultured in a sterile fermentation vessel to obtain the biomass or cell culture. During fermentation, the algae culture is aerated to promote mitochondrial respiration.

The resulting algal cell cultures or alga biomass can then be harvested and preserved according to techniques well known in the art (see for example Shelef et al. (1984), which is incorporated herein in its entirety).

In another exemplary embodiment, the resulting algae may be used to harvest lipid compositions and compounds. The methods by which such compounds and compositions may be extracted from the algae are well known in the art. In some illustrative embodiments, method are used to remove lipid compounds and compositions from wet algal biomass (an algal paste or culture that has greater than 10% moisture) or dry algal biomass (an algal paste or culture that has greater than 10% moisture). Non-limiting methods can be mechanical, chemical, supercritical or physiological.

In one exemplary embodiment, chemical solvents can be used to extract the lipid compounds and compositions. Chemical solvents are inexpensive, volatile (for ready removal later), free from toxic or reactive impurities (to avoid reaction with the lipids), able to form a two-phase system with water (to remove non-lipids), and be poor extractors of undesirable components (e.g. proteolipid protein and small molecules). Such solvents facilitate lipid compound extraction by breaking the linkages between the lipids and other non-lipid cell components without degrading the lipids. In one exemplary embodiment, the lipid compounds and compositions can be separated from algal biomass by repeatedly washing algae cells with an organic solvent. Non-limiting organic solvents include hexane, ethanol or methanol.

In further exemplary embodiments, lipid compounds and compositions can be extracted from algae by supercritical fluid extraction, which involves using supercritical fluids as a solvent to extract lipid compounds. A non-limiting example of a solvent used for supercritical extraction is carbon dioxide, which has a moderate critical temperature and pressure (31.3° C., 72.9 atm.). When raised above its critical temperature and pressure, $CO_2$ can acquire the solvating properties of a liquid while maintaining the transport properties of a gas. Lipid compounds are extracted into this supercritical fluid. Returning the superfluid to atmospheric pressure allows the solvent to assume its vapor form, so that no residues remain in the lipid compound. In the supercritical fluid/$CO_2$ extraction, $CO_2$ is liquefied under pressure and heated to the point that it has the properties of both a liquid and gas. This liquefied gas then acts as the solvent in the extracting the oil. This process may have advantages over solvent extractions, including less thermal degradation of the oil or its components (lighter appearance), oils free of solvents and oils selectively enriched for some components. Supercritical Fluid Extraction can extract almost 100% of the lipids. Supercritical extraction is an expensive process when compared to conventional solvent extraction. If the product is high value and low volume, supercritical extraction can be justified. Supercritical $CO_2$ methods also have the advantage of not utilizing synthetic chemicals to extract oil form the algal biomass. The resulting lipids can be considered free of chemical additives when a juice based medium as described herein is used for its production.

In another exemplary embodiment, the lipid compounds and compositions can be extracted by mechanical oil extraction, which involves physically disrupting the algal membrane to release lipid compounds and compositions. Non-limiting examples of mechanical oil extraction include pressing, milling, homogenization and ultrasonic-assisted extraction (cavitation).

In another exemplary embodiment, the lipid compounds and compositions can be extracted by physiological oil extraction, which involves disrupting the physiological integrity of algal cells. Non-limiting examples include enzymatic degradation of the cell membrane and osmotic shock, methods that destroy the cell wall membrane to release lipid compounds. Osmotic shock involves quickly lowering the osmotic pressure of the culture medium to induce cell wall lysis.

In another illustrative embodiment, the extraction can be performed using ultrasonic-assisted extraction. Ultrasonic extraction can greatly accelerate extraction processes. Using an ultrasonic reactor, ultrasonic waves are used to create cavitation bubbles in a solvent material. When these bubbles collapse near the cell walls, it creates shock waves and liquid jets that cause those cells walls to break and release their contents. Sonochemistry is one of the most efficient processes for inducing molecules with energy. Sonochemistry uses ultrasonic irradiation to form acoustic cavitation: the formation, growth, and implosive collapse of bubbles in a liquid. Acoustic cavitation produces local conditions of 5000K and 1000 atm. During the cavitation process, heating and cooling rates exceed 10e9 K/Hz where liquid jet streams of 400 km/hr occur.

Mechanical disruption, solvent extraction and extraction by supercritical fluids require that the algae biomass is first dried to low percentage moisture, <10% prior to processing. Other methods such as enzymatic and osmotic cell disruption, may not require a pre-drying step.

In one exemplary embodiment, the algal biomass is freeze dried, followed by solvent extraction of the lipid compounds and compositions. The freezing process consists of freezing the material. In a lab, this is often done by placing the material in a freeze-drying flask and rotating the flask in a bath, called a shell freezer, which is cooled by mechanical refrigeration, dry ice and methanol, or liquid nitrogen. On a larger-scale, freezing is usually done using a commercial freeze-dryer. In this step, it is important to cool the material below its eutectic point, the lowest temperature at which the solid and liquid phase of the material can coexist. This ensures that sublimation rather than melting will occur in the following steps. Larger crystals are easier to freeze dry. To produce larger crystals the product should be frozen slowly or can be cycled up and down in temperature. This cycling process is called annealing. However, in the case of food, or objects with formerly living cells, large ice crystals will break the cell walls. As discovered by Clarence Birdseye, when food is frozen at −40° C. to −45° C. or below, then it tastes better. Usually, the freezing temperatures are between −50° C. and −80° C. The freeze-dried algae is then subjected to progressively more polar solvents to completely fractionate the lipids present.

In another embodiment subcritical water extraction can be used with fruit juice solvent to stabilize the PUFAs during the extraction process.

Example 1

Nitrogen Content of Juices

Total bioavailable nitrogen including primary amino nitrogen (including L-arginine and glutamic acid), urea and ammonia were measured using K-PANOPA, K-Large and K-Glut biochemical kits (Megazyme, Ireland). Five juices were tested: fermented, certified organic beet juice, tomato juice, certified organic carrot juice, certified organic apple juice, and coconut water. Each juice was pasteurized, diluted to 10% concentration (vol/vol) and then tested. Reported values are adjusted for 100% juice.

TABLE 1

| Juice Type (100%) | L-glutamic acid (mg Nitrogen/L) | Primary amino nitrogen (PAN, includes L-glutamic acid and L-arginine) (mg Nitrogen/L) | Total Bioavailable Nitrogen (PAN, ammonia and urea) (mg Nitrogen/L) |
|---|---|---|---|
| Fermented Beet | 54.14 ± 0.62% | 400.90 ± 1.37% | 739.42 ± 1.26% |
| Tomato | 220.42 ± 3.49% | 619.51 ± 2.22% | 808.86 ± 2.62% |
| Carrot | 30.35 ± 10.78% | 242.61 ± 0.76% | 333.79 ± 1.41% |
| Coconut | 1.91 ± 1.57% | 43.46 ± 10.55% | 43.46 ± 10.55% |
| Apple | 16.78 ± 1.43% | 112.23 ± 7.36% | 112.23 ± 7.36% |

The pasteurized juices tested contain different nitrogen profiles. Beet juice, tomato juice and carrot juice had the highest total bioavailable nitrogen. Apple juice and coconut water had the lowest bioavailable nitrogen.

Example 2

Growth of *A. Limacinum* in Juice Media Containing Sea Water with No pH Adjustment

*A. limacinum* was propagated in juice media with no pH adjustment. A total of fifteen (15) media (used to both inoculate and culture the algae) were prepared, having the following respective juice concentrations: (1) certified organic beet juice at 10% concentration; (2) certified organic beet juice at 25% concentration; (3) certified organic beet juice at 50% concentration; (4) certified organic apple juice at 10% concentration; (5) certified organic apple juice at 25% concentration; (6) certified organic apple juice at 50% concentration; (7) tomato juice at 10% concentration; (8) tomato juice at 25% concentration; (9) tomato juice at 50% concentration; (10) coconut water at 10% concentration; (11) coconut water at 25% concentration; (12) coconut water at 50% concentration; (13) certified organic carrot juice at 10% concentration; (14) certified organic carrot juice at 25% concentration; and (15) certified organic carrot juice at 50% concentration. Each medium additionally contained sea water having a salinity of 12.7 ppt. The media were sterilized by pasteurization.

TABLE 2

Starting pH of Juice Media

| Juice Type adjusted to 12.7 ppt. salinity | pH |
|---|---|
| 10% Apple Juice | 3.61 |
| 25% Apple Juice | 3.46 |
| 50% Apple Juice | 3.38 |
| 10% Beet Juice | 4.18 |
| 25% Beet Juice | 4.08 |
| 50% Beet Juice | 4.1 |
| 10% Carrot Juice | 4.17 |
| 25% Carrot Juice | 4.09 |
| 50% Carrot Juice | 4.1 |
| 10% Coconut Water | 6.7 |
| 25% Coconut Water | 6.17 |
| 50% Coconut Water | 5.78 |
| 10% Tomato Juice | 4.1 |
| 25% Tomato Juice | 4.1 |
| 50% Tomato Juice | 4.11 |

TABLE 3

Growth maxima parameters for *A. limacinum* in juice
media with no pH adjustment

| Juice Type | Percentage % | Maximum Density cells/ml culture medium | Hour to reach maximum density (h) |
|---|---|---|---|
| Tomato | 25 | 5.13E+07 | 22 |
| Beet | 25 | 4.33E+07 | 95 |
| Carrot | 50 | 5.57E+07 | 95 |
| Coconut | 50 | 2.68E+07 | 137 |
| Apple | 50 | 7.59E+06 | 22 |

Figure 1B:
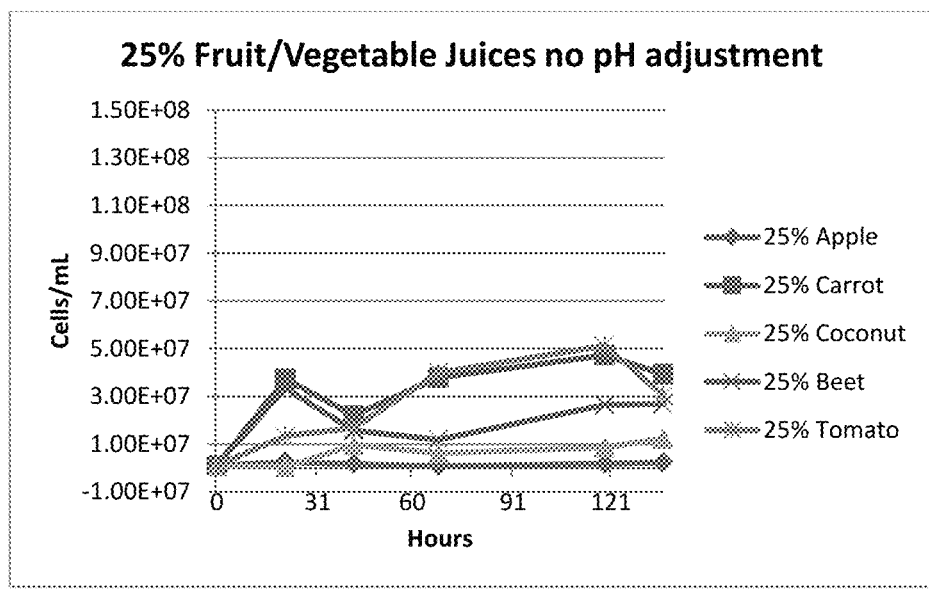
Figure 1C:
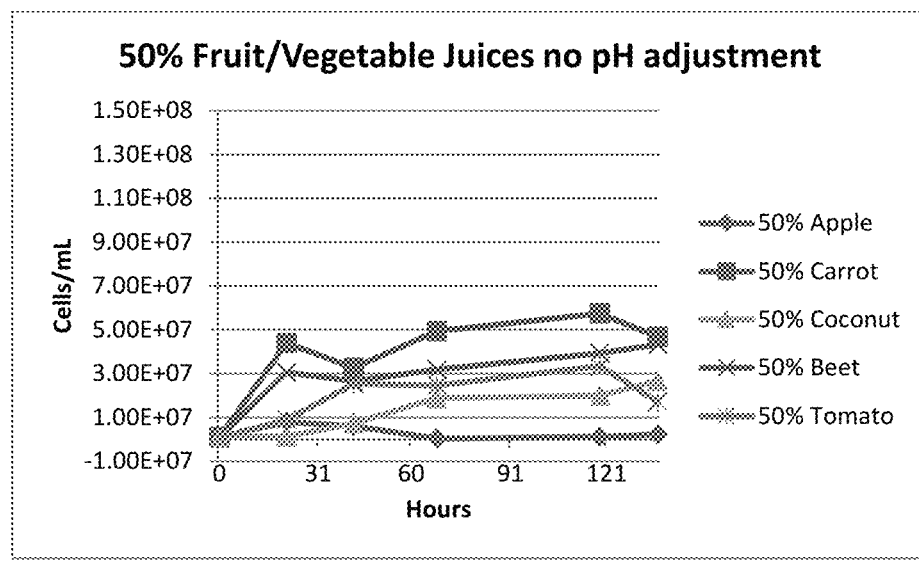

The results are presented in FIGS. 1A-1C. When juices were not pH adjusted, the media containing tomato, beet and carrot juice, respectively, yielded greater biomass as compared to media containing apple and coconut water, respectively. In addition, algae grown in a tomato juice based medium reached maximum density after 22 hours while algae grown in a coconut water based medium took the most time, 137 hours, to reach maximum density.

Example 3

Growth of *A. Limacinum* in Juice Media
Containing Sea Water and Adjusted to pH 6.8

*A. limacinum* was propagated in juice media adjusted to a pH of 6.8. A total of fifteen (15) media (used to both inoculate and culture the algae) were prepared, having the following respective juice concentrations: (1) certified organic beet juice at 10% concentration; (2) certified organic beet juice at 25% concentration; (3) certified organic beet juice at 50% concentration; (4) certified organic apple juice at 10% concentration; (5) certified organic apple juice at 25% concentration; (6) certified organic apple juice at 50% concentration; (7) tomato juice at 10% concentration; (8) tomato juice at 25% concentration; (9) tomato juice at 50% concentration; (10) coconut water at 10% concentration; (11) coconut water at 25% concentration; (12) coconut water at 50% concentration; (13) certified organic carrot juice at 10% concentration; (14) certified organic carrot juice at 25% concentration; and (15) certified organic carrot juice at 50% concentration. Each medium additionally contained sea water, sufficient to obtain a salinity of 12.7 ppt. The media were sterilized by pasteurization.

TABLE 3

Growth Maxima parameters for *A. limacinum* in juice
media adjusted to pH 6.8

| Juice Type | Percentage % | Maximum Density cells/ml culture medium | Hour to reach maximum density (h) |
|---|---|---|---|
| Tomato | 50 | 1.07E+08 | 22 |
| Beet | 25 | 1.07E+08 | 95 |
| Carrot | 50 | 6.00E+07 | 45 |
| Coconut | 50 | 3.88E+07 | 95 |
| Apple | 50 | 1.28E+07 | 22 |

Figure 2A:
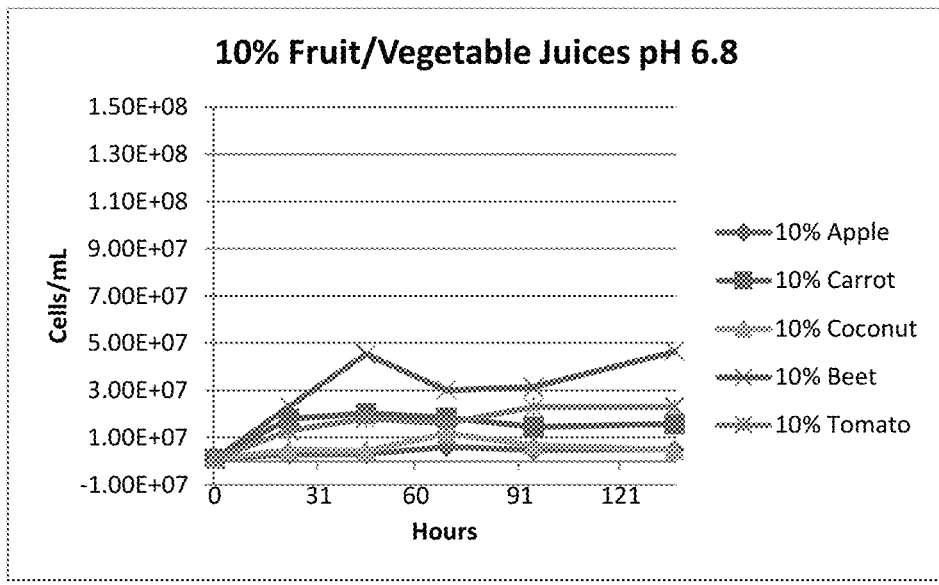
FIGS. 2A-2C are line graphs showing the growth of *A. limacinum* in juice media and seawater with pH adjusted to 6.8.
Figure 2B:
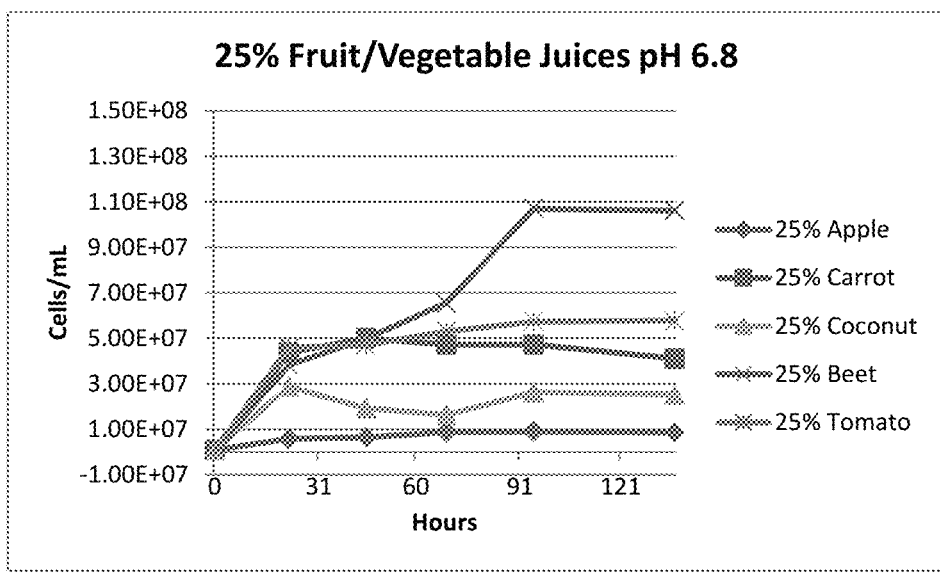
Figure 2C:
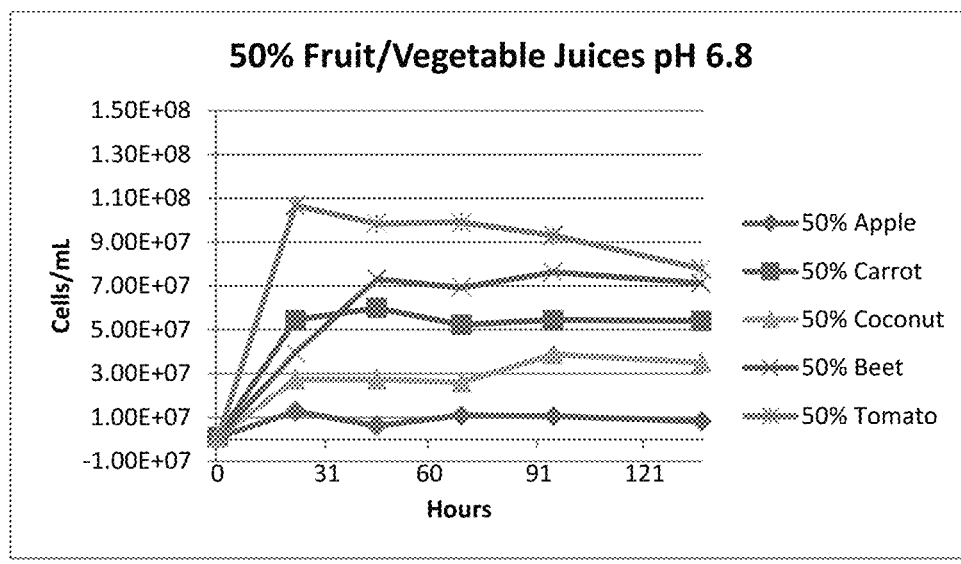

The results are presented in FIGS. 2A-2C. At pH 6.8, media containing tomato juice at 50% concentration and beet juice at 25% concentration, respectively, yielded the highest algal biomass. Cell growth rate was the fastest in tomato juice based media: it took 22 hours to reach maximum density. Tomato juice contained the highest content of natural glutamic acid, which could have contributed to the faster growth rate. Coconut water and apple juice based media yielded the lowest biomass. It is reported that pH can impact the dissociation rate of glutamic acid, thus impacting the bioavailability of nitrogen, especially when in the form of glutamic acid (Ault, A. (2004) "The monosodium glutamate story: The commercial production of MSG and other amino acids" Journal of Chemical Education). At higher pH, more glutamic acid is bioavailable so that biomass is increased for each media formulation, especially those with higher concentrations of glutamic acid, such as tomato and beet juice based media.

Example 4

Growth of *A. Limacinum* in Juice Media
Supplemented with Dextrose

*A. limacinum* was propagated in juice media supplemented with dextrose. A total of five (5) media (used to both inoculate and culture the algae) were prepared, having the following respective juice concentrations: (1) certified organic beet juice at 25% concentration; (2) tomato juice at 50% concentration; (3) certified organic carrot juice at 50% concentration; (4) certified organic apple juice at 50% concentration; and (5) coconut water at 50% concentration. Each medium was supplemented with dextrose to a concentration of 6%. The media were sterilized by pasteurization.

TABLE 4

Growth maxima parameters for *A. limacinum* grown in
media supplemented with dextrose

| Juice Type | Percentage % | Maximum Density cells/ml culture medium | Maximum Density g/L dry cell weight | Hour to reach maximum density (h) |
|---|---|---|---|---|
| Tomato | 50 | 9.08E+07 | 30.36 | 50 |
| Beet | 50 | 9.83E+07 | 30.38 | 97 |
| Carrot | 50 | 6.88E+07 | 16.64 | 97 |
| Coconut | 50 | 4.23E+07 | NA | 97 |
| Apple | 50 | 4.28E+06 | NA | 120 |

Figure 3A:
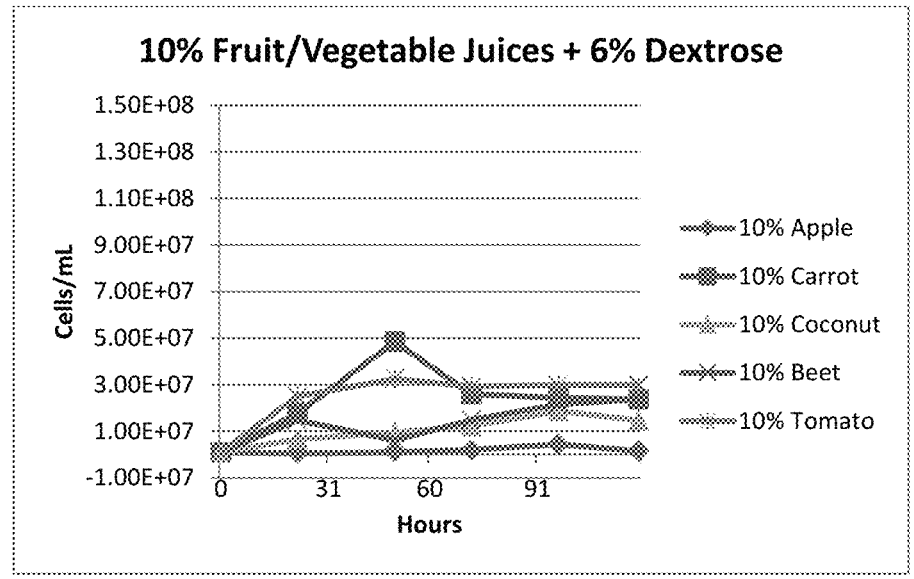
FIGS. 3A-3C are line graphs showing the growth of *A. limacinum* in juice media and seawater with pH adjusted to 6.8 and supplemented with dextrose.
Figure 3B:
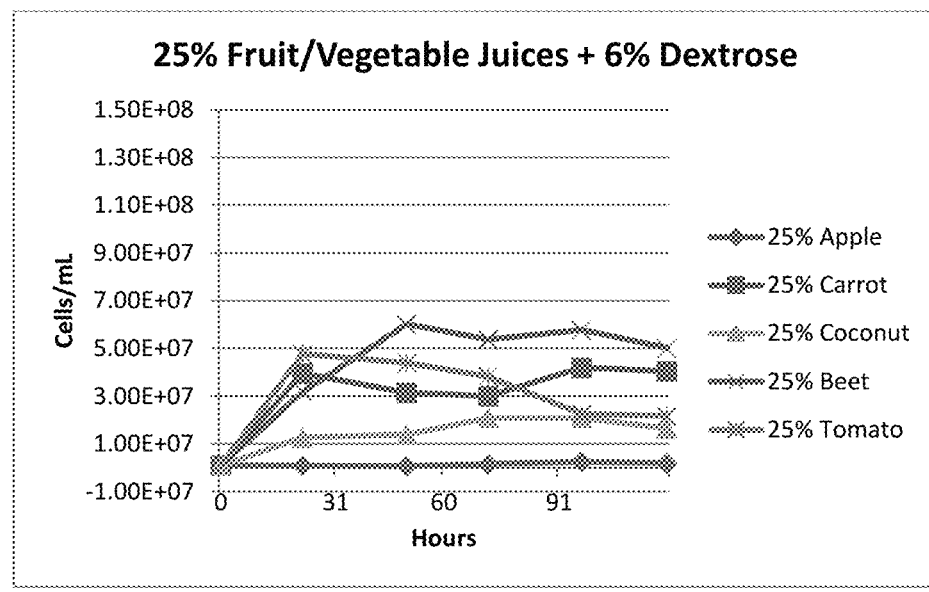
Figure 3C:
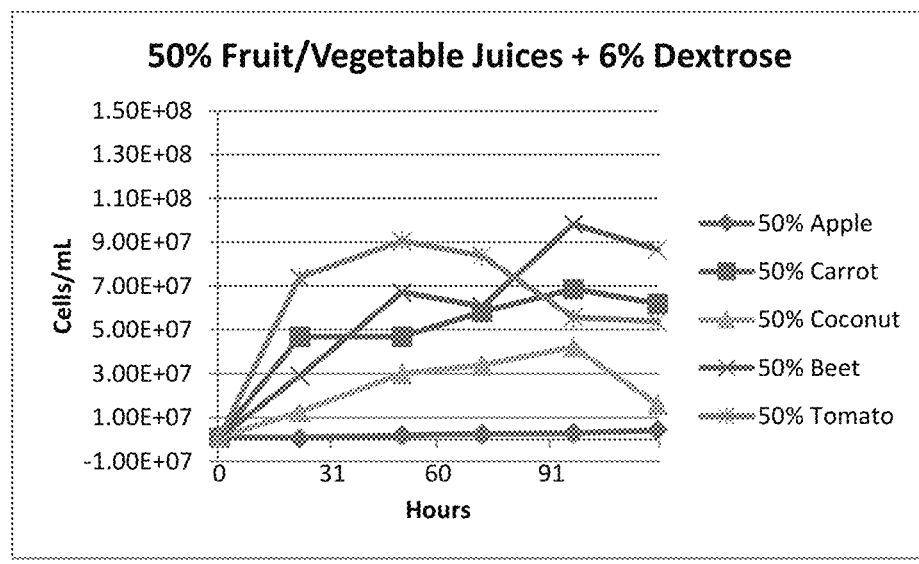

The results are presented in FIGS. 3A-3C. *A. limacinum* cells grown in media containing tomato, beet and carrot juice at 50%, 25% and 50% concentrations, respectively, yielded the highest biomass, 9.0 E+07, 9.83 E+07 and 6.88 E+07, respectively. In contrast, algal cells grown in media containing coconut water and apple juice, respectively, yielded the lowest biomass, 4.23 E+07 and 4.28 E+06, respectively. *A. limacinum* grown in medium containing 50% tomato juice supplemented with dextrose reached maximum density most quickly, after 50 hours of growth.

Example 5

Dha Yield from *A. Limacinum* Culture Grown in
Juice Media

*A. limacinum* was grown in various juice media. A total of fifteen (15) media (used to both inoculate and culture the algae) were prepared, having the following respective juice concentrations: (1) certified organic beet juice at 10% concentration; (2) certified organic beet juice at 25% concentration; (3) certified organic beet juice at 50% concentration;

(4) certified organic apple juice at 10% concentration; (5) certified organic apple juice at 25% concentration; (6) certified organic apple juice at 50% concentration; (7) tomato juice at 10% concentration; (8) tomato juice at 25% concentration; (9) tomato juice at 50% concentration; (10) coconut water at 10% concentration; (11) coconut water at 25% concentration; (12) coconut water at 50% concentration; (13) certified organic carrot juice at 10% concentration; (14) certified organic carrot juice at 25% concentration; and (15) certified organic carrot juice at 50% concentration. Each medium additionally contained sea water having a salinity of 12.7 ppt and was supplemented with certified organic dextrose at a concentration of 6%. The media were sterilized by pasteurization.

Algal cells were dried by vacuum filtration and samples were transesterified in situ. DHA was quantified by gas chromatography by comparison to internal and external standards.

TABLE 5

Maximum DHA Yield for Juice Based Media (Having a 50% Juice Concentration)

| Juice Formulation | DHA yield mg/ml | Hour harvested (h) |
|---|---|---|
| 50% Beet | 4.4 | 120 |
| 50% Tomato | 5.0 | 72 |
| 50% Carrot | 1.7 | 72 |
| 50% Coconut | 0.7 | 72 |
| 50% Apple | 0.3 | 72 |

Figure 4:
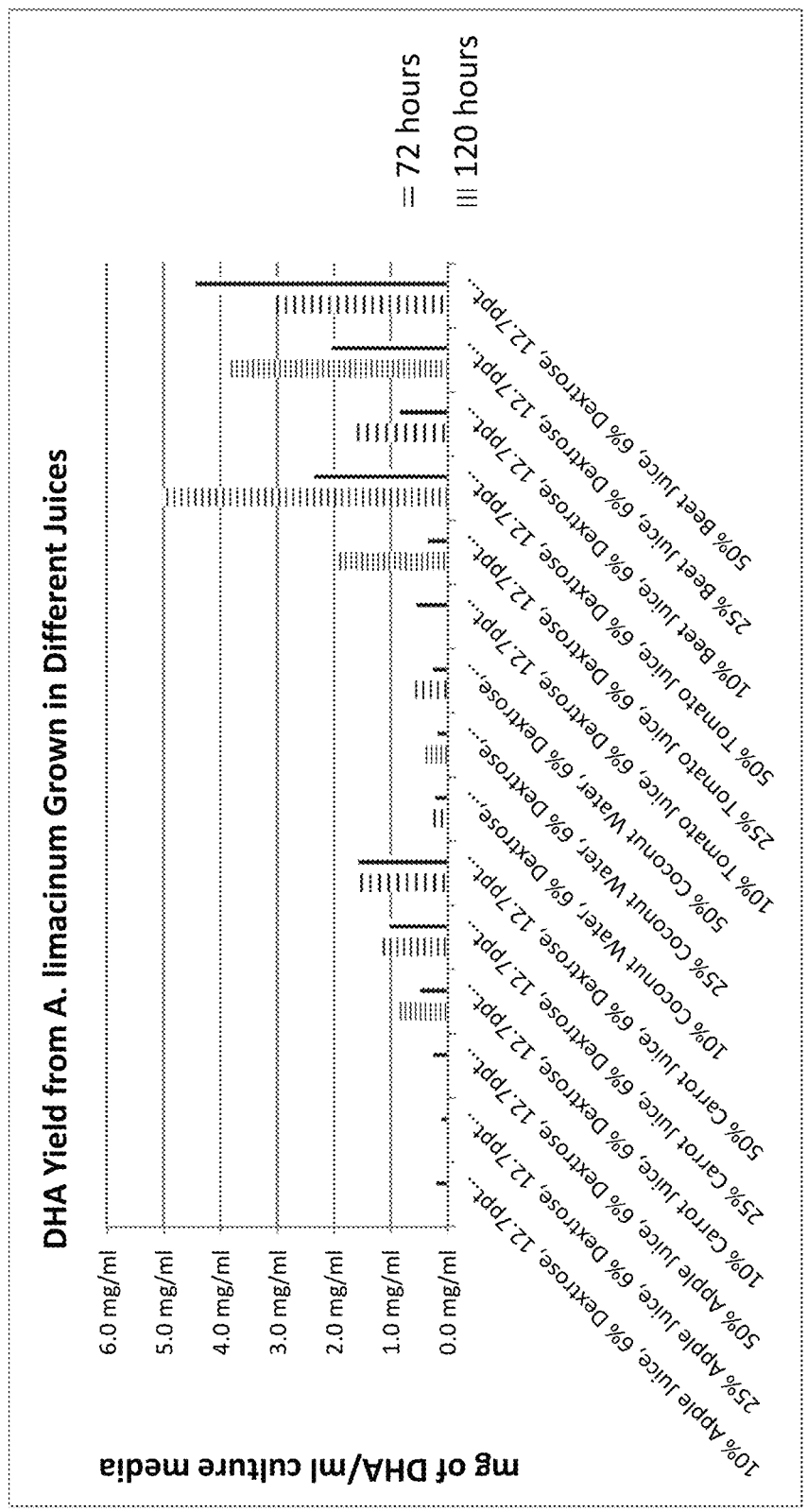
FIG. 4 is a bar graph that shows DHA yield from an *A. limacinum* culture grown in juice media containing sea water and supplemented with dextrose (mg/ml culture medium).

The results are presented in FIG. 4. DHA yield per ml of media was the highest for certified organic dextrose supplemented media containing 50% concentration tomato juice and 50% concentration beet juice, 5.0 mg DHA/L juice medium and 4.4 mg DHA/L juice medium, respectively.

Example 6

Epa Yield from *A. Limacinum* Culture Grown in Juice Media

*A. limacinum* was grown in various juice media. A total of fifteen (15) media (used to both inoculate and culture the algae) were prepared, having the following respective juice concentrations: (1) certified organic beet juice at 10% concentration; (2) certified organic beet juice at 25% concentration; (3) certified organic beet juice at 50% concentration; (4) certified organic apple juice at 10% concentration; (5) certified organic apple juice at 25% concentration; (6) certified organic apple juice at 50% concentration; (7) tomato juice at 10% concentration; (8) tomato juice at 25% concentration; (9) tomato juice at 50% concentration; (10) coconut water at 10% concentration; (11) coconut water at 25% concentration; (12) coconut water at 50% concentration; (13) certified organic carrot juice at 10% concentration; (14) certified organic carrot juice at 25% concentration; and (15) certified organic carrot juice at 50% concentration. Each medium additionally contained sea water having a salinity of 12.7 ppt and was supplemented with certified organic dextrose at a concentration of 6%. The media were sterilized by pasteurization.

Algal cells were dried by vacuum filtration and samples were transesterified in situ. EPA was quantified by gas chromatography by comparison to internal and external standards.

TABLE 5

Maximum EPA Yield for Juice Based Media (Having a 50% Juice Concentration)

| Juice Formulation | EPA Yield (mg/ml) | Hour Harvested (h) |
|---|---|---|
| 50% Beet | 0.039 | 120 |
| 50% Tomato | 0.035 | 72 |
| 50% Carrot | 0.012 | 120 |
| 50% Coconut | 0.004 | 72 |
| 50% Apple | 0.003 | 120 |

Figure 5:
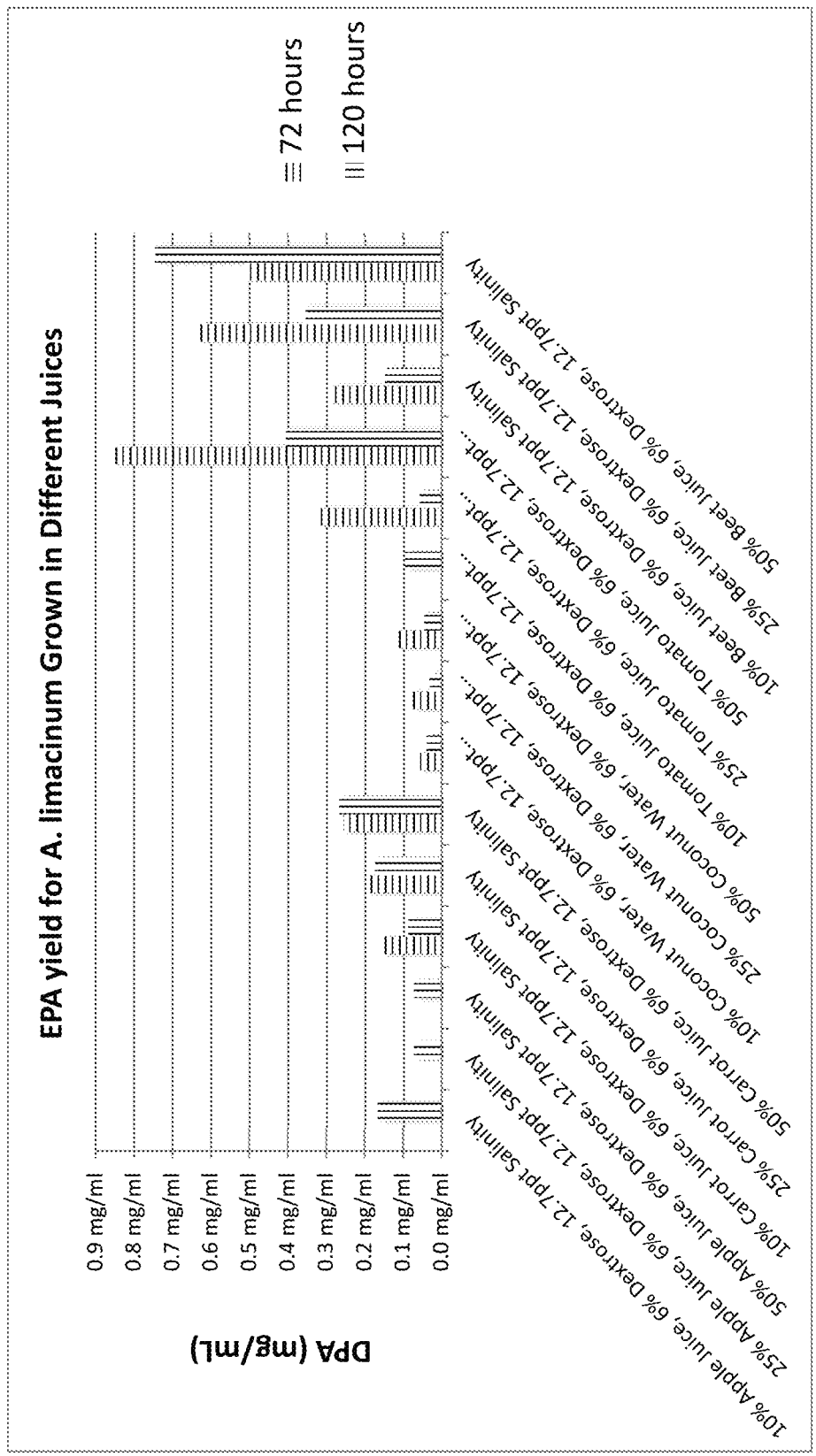
FIG. 5 is a bar graph that shows EPA yield from an *A. limacinum* culture grown in juice media containing sea water and supplemented with dextrose (mg/ml culture medium).

The results are presented in FIG. 5. EPA yield per ml of media was the highest for certified organic dextrose supplemented media containing 50% concentration tomato juice and 50% concentration beet juice, respectively.

Example 7

Dpa Yield from *A. Limacinum* Culture Grown in Juice Media

*A. limacinum* was grown in various juice media. A total of fifteen (15) media (used to both inoculate and culture the algae) were prepared, having the following respective juice concentrations: (1) certified organic beet juice at 10% concentration; (2) certified organic beet juice at 25% concentration; (3) certified organic beet juice at 50% concentration; (4) certified organic apple juice at 10% concentration; (5) certified organic apple juice at 25% concentration; (6) certified organic apple juice at 50% concentration; (7) tomato juice at 10% concentration; (8) tomato juice at 25% concentration; (9) tomato juice at 50% concentration; (10) coconut water at 10% concentration; (11) coconut water at 25% concentration; (12) coconut water at 50% concentration; (13) certified organic carrot juice at 10% concentration; (14) certified organic carrot juice at 25% concentration; and (15) certified organic carrot juice at 50% concentration. Each medium additionally contained sea water having a salinity of 12.7 ppt and was supplemented with certified organic dextrose at a concentration of 6%. The media were sterilized by pasteurization.

Algal cells were dried by vacuum filtration and samples were transesterified in situ. DPA was quantified by gas chromatography by comparison to internal and external standards.

Figure 6:
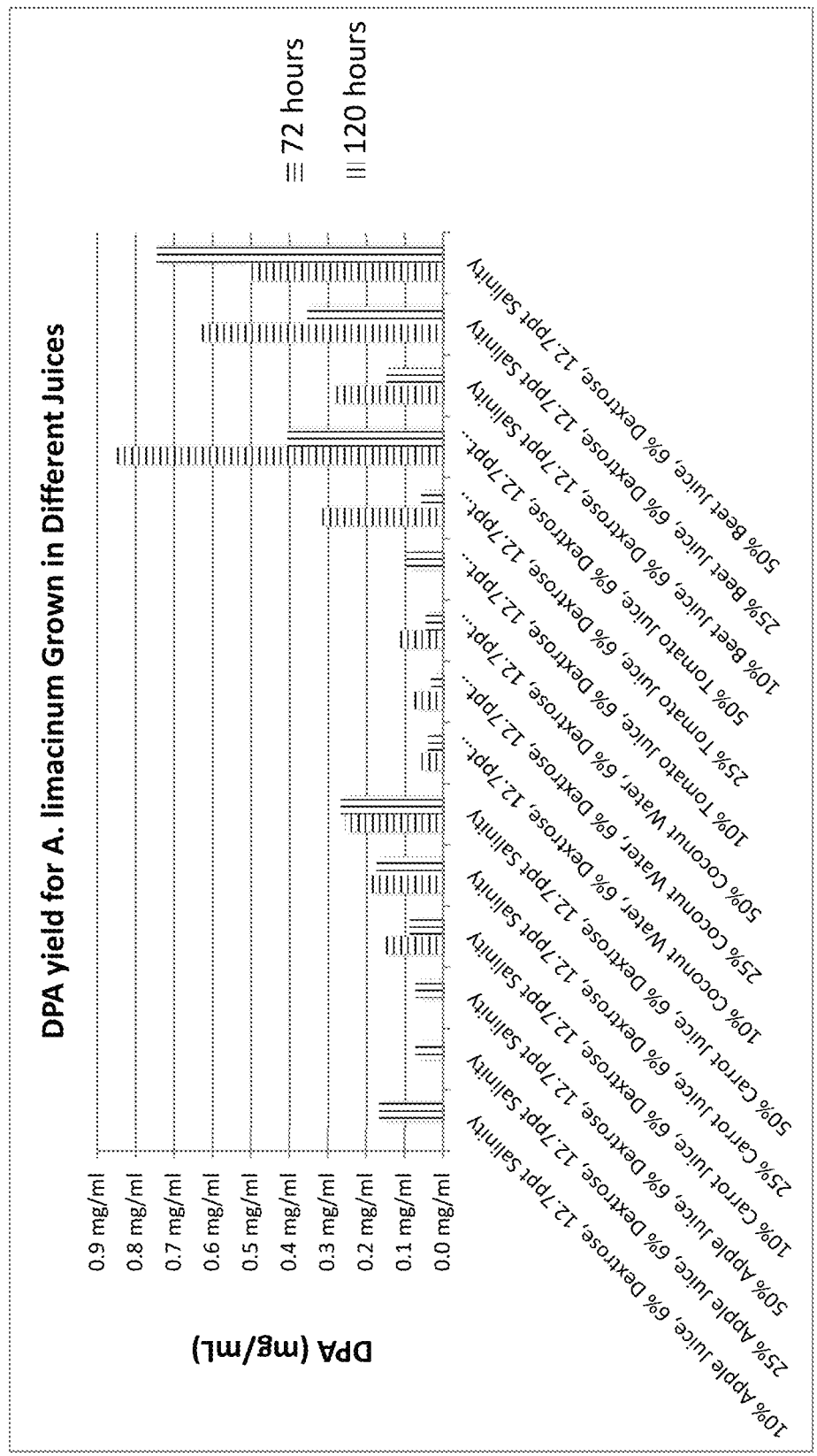
FIG. 6 is a bar graph that shows DPA extracted from an *A. limacinum* culture grown in juice media containing sea water and supplemented with Dextrose (mg/ml culture medium).

The results are presented in FIG. 6. DPA yield per ml of media was the highest for certified organic dextrose supplemented media containing 50% concentration tomato juice and 50% concentration beet juice, respectively.

TABLE 6

Maximum DPA Yield for Each Juice Type

| Juice Formulation | DPA Yield (mg/ml) | Hour Harvested (h) |
|---|---|---|
| 50% Beet | 0.75 | 120 |
| 50% tomato | 0.85 | 72 |
| 50% Carrot | 0.27 | 120 |
| 50% Carrot | 0.11 | 72 |
| 10% Apple | 0.17 | 120 |

Example 8

Growth of *Nannochloropsis Oculata* in Beet Juice Media

*N. oculata* was propagated in beet juice media. $1\times10^6$ *N. Oculata* cells were inoculated and cultured in each of the following media: (1) F/2 medium (standard synthetic commercial medium); (2) natural fermented beet juice (pH adjusted to 7.6; salinity adjusted to 25 ppt with seawater); (3) natural fermented beet juice (pH adjusted to 7.6; salinity adjusted to 25 ppt with seawater) supplemented with 30 mM dextrose; and; (4) natural fermented beet juice (pH adjusted to 7.6; salinity adjusted to 25 ppt with seawater) supplemented with 30 mM ethanol. The beet juice media were sterilized by pasteurization. Cells were incubated at 22° C. with shaking at 160 rpm for 5 days.

TABLE 7

Growth maxima parameters for *N. oculata* grown in beet juice media

| Hours | Growth in F/2 Medium (cells/ml) | Growth in 42% Beet Juice (cells/ml) | 42% Beet Juice 30 mm Dextrose (cells/ml) | 42% Beet Juice 30 mM Ethanol (cells/ml) |
|---|---|---|---|---|
| 0 | 1.00E+06 | 1.00E+06 | 1.00E+06 | 1.00E+06 |
| 24 | 1.35E+06 | 8.75E+06 | 1.23E+07 | 7.50E+06 |
| 48 | 1.55E+06 | 6.10E+06 | 4.90E+06 | 9.25E+06 |
| 72 | 2.20E+06 | 1.60E+07 | 1.08E+07 | 1.63E+07 |
| 96 | 2.50E+06 | 1.45E+07 | 1.15E+07 | 1.40E+07 |
| 120 | 3.65E+06 | 1.65E+07 | 1.13E+07 | 1.35E+07 |

Figure 7:
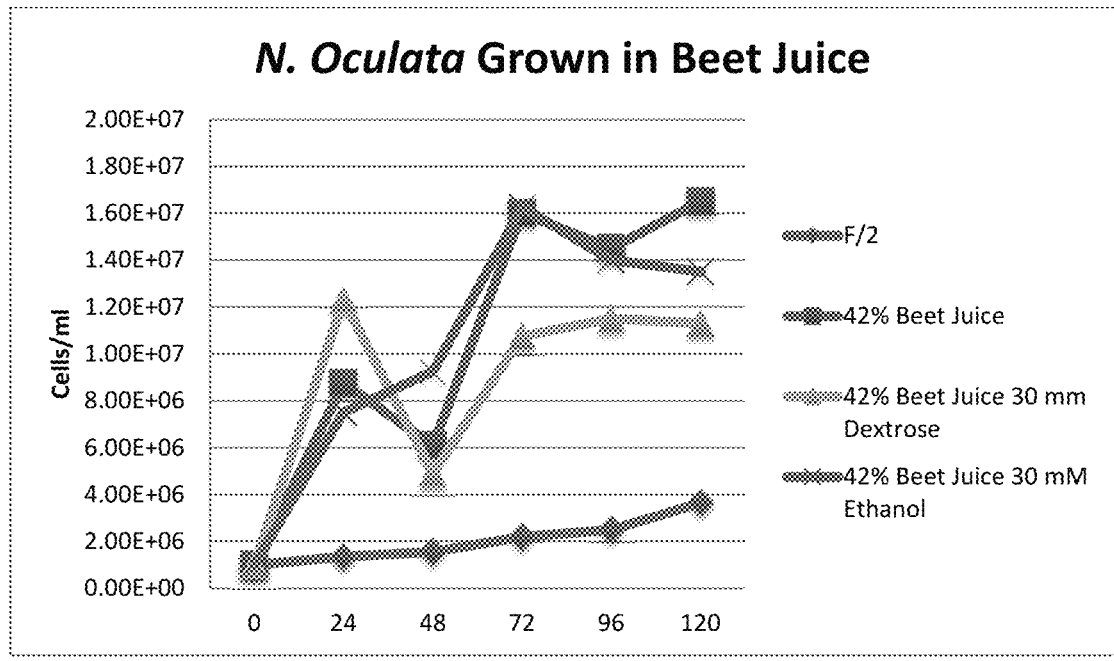
FIG. 7 is a line graph showing the growth of *N. Oculata* in beet juice media (either with or without carbon source supplementation) and F/2 medium (cells/ml culture medium).

The results are presented in FIG. 7. *N. oculata* cells grown in beet juice media yielded higher biomass as compared to *N. oculata* cells grown in commercial F/2 medium.

Example 9

Growth of *S. Limacinum* in Beet Molasses Media

*S. Limacinum* was propagated in beet molasses media. 1×10⁶ *S. Limacinum* cells were inoculated and cultured in each of the following media: (1) fermented beet juice supplemented with 6% dextrose ("BJ"); (2) organic certified 8.4% beet molasses, supplemented with 6% dextrose ("BM"); and (3) organic certified 8.4% beet molasses, hydrolyzed with the enzyme invertase ("BM-H"). The media were sterilized by pasteurization or filtration. Beet juice and beet molasses formulations were adjusted to ensure equal nitrogen content. Cells were incubated at 22° C. with shaking at 200 rpm for 5 days.

Figure 8:
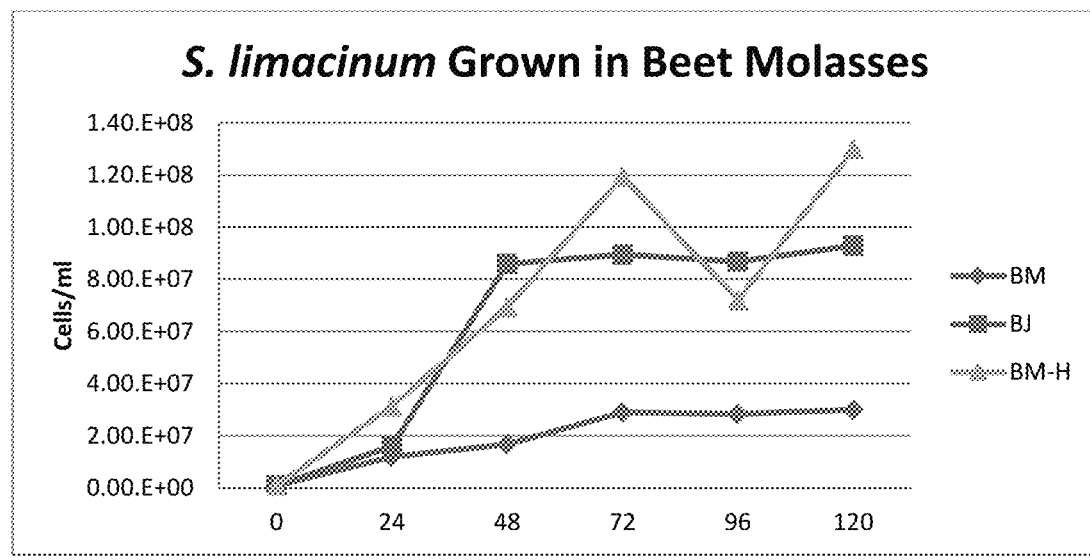
FIG. 8 is a line graph showing the growth of *S. limacinum* in beet molasses based medium (cells/ml culture medium).

The results are presented in FIG. 8. Organic certified beet molasses media can support *S. limacinum* growth. All beet media contained sufficient nitrogen to support *S. limacinum* growth; however, *S. limacinum* growth in beet molasses medium supplemented with 6% dextrose (BM) was partially inhibited. Since beet molasses already has high sugar content, the additional sugar could have inhibited *S. limacinum* growth. *S. limacinum* is not able to utilize sucrose, a major component of beet molasses; therefore, hydrolysis of sucrose was investigated so that sucrose in the beet molasses could be converted to fructose and glucose. Fructose and glucose are bioavailable forms of sugar for *S. limacinum* metabolism. In this case, the hydrolyzed beet molasses medium (BM-H) would not require dextrose supplementation. Hydrolyzed beet molasses medium (BM-H) did support *S. limacinum* growth to a similar level as compared to naturally fermented beet juice medium supplemented with 6% dextrose (BJ). Since beet juice also contains sucrose, it also can be optionally hydrolyzed to support *S. limacinum* growth.

Example 10

Hydrolysis of Beet Juice and Beet Molasses to Yield Dextrose and Fructose

Solutions containing 10% beet molasses, 20% beet molasses and 100% beet juice (pasturized (95° C.); pH 3.7), respectively, were adjusted to a pH of 4.5 using food grade organic acids and treated with Invertase from baker's yeast (Sigma-Chemical Co.) under sterile conditions. A K-SU-FRG kit (Megazyme, Ireland) was used to analyze the solutions to determine sucrose, fructose and glucose concentrations in each formulation before and after enzyme treatment. Samples were spiked with glucose, fructose and sucrose standards. The solutions were incubated at 55° C. for 24 hrs. The results are presented in Table 8.

TABLE 8

Hydrolysis of Beet Juice and Beet Molasses to Yield Dextrose and Fructose

| Sample | D-glucose (g/L) | Sucrose (g/L) | D-fructose (g/L) | Hydrolysis efficiency (%) |
|---|---|---|---|---|
| 4.7% sucrose solution | | 5.92 | | |
| 4.7% sucrose solution after hydrolysis | 3.84 | | 3.87 | 65.17 |
| 9.4% sucrose solution | | 7.89 | | |
| 9.4% sucrose solution after hydrolysis | 6.64 | | 6.91 | 85.88 |
| 10% beet molasses solution | | 5.13 | | |
| 10% beet molasses solution after hydrolysis | 3.94 | | 3.98 | 77.23 |
| 20% beet molasses solution | 0.42 | 8.28 | | |
| 20% beet molasses solution after hydrolysis | 6.44 | | 6.49 | 78.01 |
| 100% pasteurized beet juice (95 C., pH 3.7) | 8.51 | 52.99 | 7.47 | |
| 100% pasteurized beet juice after hydrolysis | 55.78 | | 52.89 | 87.45 |

The efficiency of hydrolysis in 10% beet molasses solution, 20% beet molasses solution and 100% beet juice were found to be 77%, 78% and 87%, respectively.

Example 11

Dha Yield from *A. Limacinum* Culture Grown in Beet Molasses Media

*S. Limacinum* was propagated in beet molasses media. 1×10⁶ *S. Limacinum* cells were inoculated and cultured in each of the following media: (1) commercial basal medium (3% dextrose, 1% yeast extract and seawater); (2) fermented beet juice supplemented with 6% dextrose; (3) 8.4% beet molasses supplemented with 6% dextrose; and (4) 8.4% beet molasses hydrolyzed with the enzyme invertase. The media were sterilized by pasteurization or filtration. Beet juice and beet molasses formulations were adjusted to ensure equal nitrogen content. Cells were incubated at 22° C. with shaking at 200 rpm for 5 days. A volume of culture containing an equivalent number of cells (2×10⁸ cells) was harvested for each medium after 120 hours of growth. The culture samples were freeze-dried and DHA content was determined by gas chromatography using standard methods. The results are presented in Table 9.

TABLE 9

Maximum DHA Yield for Molasses Based Media

| Media Formulation | DHA mg/2 × $10^8$ cells 120 hours |
|---|---|
| Basal Medium, 3% Dextrose | 1.99 |
| Beet Molasses Medium-Non-hydrolyzed, 6% Dextrose | 0.00 |
| Beet Molasses Medium-Hydrolyzed | 4.11 |
| Fermented Beet Juice Medium, 6% dextrose | 9.11 |

Molasses medium hydrolyzed with invertase can support *S. limacinum* growth and yields higher DHA per ml of medium as compared to the commercial basal medium.

Example 12

Growth of, and Dha Yield from, *A. Limacinum* Culture Grown in Beet Juice Media Supplemented with Dextrose and Yeast Extract

TABLE 10

Impact of combined yeast extract supplementation and sugar supplementation on *S. limacinum* growth in pasteurized beet juice medium

| Medium*- | Hours of Growth | | | | |
|---|---|---|---|---|---|
| Replicates | 0 | 24 | 48 | 72 | 96 |
| 1-A | 1.00E+06 | 1.06E+08 | 1.18E+08 | 1.31E+08 | 1.46E+08 |
| 2-A | 1.00E+06 | 1.05E+08 | 7.10E+07 | 2.02E+08 | 1.61E+08 |
| 3-A | 1.00E+06 | 9.90E+07 | 1.09E+08 | 1.22E+08 | 1.53E+08 |
| 3-B | 1.00E+06 | 8.25E+07 | 8.25E+07 | 1.45E+08 | 1.19E+08 |
| 3-C | 1.00E+06 | 8.25E+07 | 1.08E+08 | 1.50E+08 | 1.10E+08 |
| 3-D | 1.00E+06 | 8.10E+07 | 1.17E+08 | 1.46E+08 | 9.65E+07 |
| 4-A | 1.00E+06 | 9.05E+07 | 8.15E+07 | 1.33E+08 | 1.43E+08 |
| 5-A | 1.00E+06 | 8.00E+07 | 1.08E+08 | 8.80E+07 | 1.10E+08 |

*1 (60% Pasteurized Beet Juice {BJ}, 2% Dextrose {D}, 0.1% Yeast Extract {YE}), 2 (60% BJ, 2% D, 1% YE), 3 (60% BJ, 4% D, 0.55% YE), 4 (60% BJ, 6% D, 0.1% YE), 5 (60% BJ, 6% D, 1% YE)

TABLE 11

Impact of combined yeast extract supplementation and sugar supplementation on DHA production in *S. limacinum* in pasteurized beet juice medium

| Medium*- | DHA mg/2 × $10^8$ | Harvest time (hours after culture inoculation) | | |
|---|---|---|---|---|
| Replicates | cells/ml | 48 | 72 | 96 |
| 1-A | | 3.40 | 2.62 | 1.31 |
| 2-A | | 3.85 | 0.99 | 3.75 |
| 3-A | | 3.47 | 4.94 | 7.47 |
| 3-B | | 4.03 | 4.03 | 8.71 |
| 3-C | | 4.46 | 5.06 | 7.90 |
| 3-D | | 5.58 | 4.31 | 8.54 |
| 4-A | | 5.38 | 4.89 | 10.01 |
| 5-A | | 3.16 | 9.99 | 15.61 |

*1 (60% Pasteurized Beet Juice {BJ}, 2% Dextrose {D}, 0.1% Yeast Extract {YE}), 2 (60% BJ, 2% D, 1% YE), 3 (60% BJ, 4% D, 0.55% YE), 4 (60% BJ, 6% D, 0.1% YE), 5 (60% BJ, 6% D, 1% YE)

Statistical experimental design was employed to assess the impact of multiple variables on *S. limacinum* biomass and DHA production in pasteurized beet juice medium. In this study the combined impact of adding yeast extract (a source of vitamins) and sugar (required for omega-3 fatty acid production) was assessed. To examine these two variables for their combined impact on DHA and *S. limacinum* biomass production, a 2-factor, 3-level fractional factorial design was implemented. Since two-level factorial designs quickly become too large for practical application as the number of variables increase a fractional design was selected. To estimate the experimental errors, four centre points in which factors were set at their midpoint, were included. This design (Table 12) was generated by the principles of RSM using Commercial software, Design Expert Modde 9.0 (Stat-Ease Inc.; Minneapolis, Minn.). To support this design, three, yeast extract concentrations, 0.1%, 0.55% and 1% (Factor1, $X_1$) were assessed. In addition three sugar concentrations were assessed, 2%, 4% and 6% dextrose (Factor2, $X_2$). The responses being monitored were the biomass (CFU/mL, $Y_1$) and the DHA content (mg DHA/2×$10^8$ cells, $Y_2$). Based on the experimental values ($Y_1$, $Y_2$) the model coefficients were estimated, from which the variable's effects or degree of influence of variables on each response were estimated, using a Pareto chart. The lack of fit for the three models was statistically determined as well.

TABLE 12

Fractional factorial design arrangement of the actual and coded experimental values for the growth of *S. limacinum* in beet juice media supplemented with yeast extract and dextrose.

| | Dextrose | | Yeast Ext. | |
|---|---|---|---|---|
| Run | Coded | Actual (%) | Coded | Actual (%) |
| 1 | 0 | 4 | 0 | 0.55 |
| 2 | 0 | 4 | 0 | 0.55 |
| 3 | 0 | 4 | 0 | 0.55 |
| 4 | −1 | 2 | −1 | 0.1 |
| 5 | −1 | 2 | 1 | 1 |
| 6 | 0 | 4 | 0 | 0.55 |
| 7 | 1 | 6 | −1 | 0.1 |
| 8 | 1 | 6 | 1 | 1 |

Figure 9:
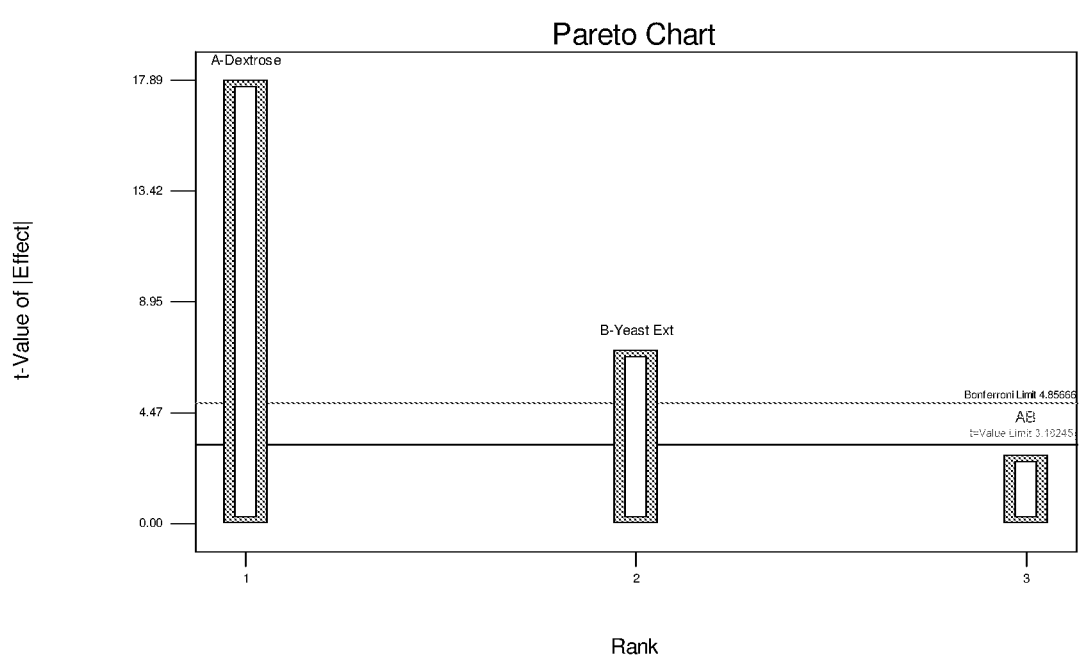
FIG. 9 is a Pareto Chart showing the DHA content of *S. limacinum* biomass grown in beet juice based medium supplemented with dextrose and/or yeast extract.

The DHA content (mg DHA/2×$10^8$ cells, $Y_2$) was monitored at 48, 72 and 96 hrs of cell growth (Table 11). The values obtained at the 96 hr time point were found to be the most significant for DHA production. Hence the experimental data obtained at 96 hr were further evaluated using response surface methodology. Based on the ANOVA analysis, the model (DHA) F-value of 113.47 implies that the model is significant. The lack of fit value of 0.3184 also implies that the lack of fit relative to the pure error was not significant. In addition the "Pred R-Squared" of 0.87 was in reasonable agreement with the "Adj R-Squared" of 0.98. Based on the ANOVA analysis the probability value for each individual term in the model was obtained and as a result it was observed that both factors including Dextrose concentration (Prob>F, <0.0001) and Yeast extract concentration (Prob>F, 0.0027) significantly affected the DHA content of the cells. The Pareto-style leffectl plot (FIG. 9) represents a graphical representation of these ordered estimates, from the largest to the smallest. As FIG. 9 shows the DHA content is positively affected by both yeast extract and dextrose addition. The most significant factor is dextrose concentration with a contribution of 84.01% as opposed to a 12.85% contribution of the yeast extract concentration. This is expected since it is likely that the dextrose carbon chain is required as a building block for DHA production.

Because cells are in very late stationary phase at 96 hours it was decided that the 72 hour data point was more relevant to assess the impact of the two factors on biomass. Based on the ANOVA analysis for the fitted model for the Biomass (CFU/mL, $Y_1$) data, the model F-value of 18.0 implies that the model is significant. The lack of fit value of 0.7975 also implied that the lack of fit relative to the pure error was not significant. The "Pred R-Squared" of 0.85 was in reasonable agreement with the "Adj R-Squared" of 0.88. Based on the ANOVA analysis and the Pareto-style Chart it was observed that the biomass was significantly negatively affected by dextrose concentration (43.72% contribution). Yeast extract did not have a significant effect on biomass (2.47% contribution). However the interaction of dextrose and yeast extract concentration showed a significantly negative effect on the biomass (46.91% contribution). This is expected since it is reported that high sugar concentration can inhibit *S. limacinum* growth.

The correlation between DHA synthesized by the cells and the biomass was also investigated. More than 0.85% negative correlation was observed. To summarize the results observed, natural beet juice can be supplemented with yeast extract and dextrose to significantly increase DHA yield in *S. limacinum*. Dextrose Concentration has the greatest positive impact on DHA content per cell and a negative impact on cell biomass at the concentrations tested.

Example 13

Nitrogen Content of Beet Molasses and Other Juices

Total bioavailable nitrogen including primary amino nitrogen (including L-arginine and glutamic acid), urea and ammonia were measured using K-PANOPA, K-Large and K-Glut biochemical kits (Megazyme, Ireland). Beet molasses was tested. The sample was diluted to 10% concentration (vol/vol) and then tested. Reported values are adjusted for 100% juice. The results are summarized in Table 13.

TABLE 13

Nitrogen Concentration of Beet Molasses

| Juice Type (100%) | L-glutamic acid (mg Nitrogen/L) | Primary amino nitrogen (PAN, includes L-glutamic acid and L-arginine) (mg Nitrogen/L) | Total Bioavailable Nitrogen (PAN, ammonia and urea) (mg Nitrogen/L) |
|---|---|---|---|
| Beet Molasses | 1.81 ± 0.2% | 2273.04 ± 14.79% | 2990.68 ± 14.85% |

Beet molasses has a high concentration of total bioavailable nitrogen>2990 mg Nitrogen/L.

Example 14

Growing Algae in Juice Based Media Improves Fatty Acid Stability

*S. limacinum* was inoculated into a tomato juice based medium. Equal volumes of the culture were centrifuged and the medium was decanted. The resulting algae pellets were each individually suspended in beet juice, carrot juice, blueberry juice or water at a ratio of 9:1. An ~0.8 g sample of each mixture was tested to determine the starting DHA concentration. Additional ~0.8 g samples were separated into aliquots, sealed in 1.5 ml tubes and then heated at 60° C. for up to six days. DHA levels were quantified by gas chromatography of FAMEs. The results are summarized in Table 14.

TABLE 14

Juices can protect DHA from oxidation in *S. limacinum* algae biomass or paste

| Sample Descriptions | Starting DHA Concentration (mg/g) WCW | DHA Concentration after 6 days incubation at 60° C. (mg/g) WCW | % DHA Oxidized |
|---|---|---|---|
| Beet Juice, Algae suspension 9:1 | 2.07 | 1.83 | 11.59 |
| Carrot Juice, Algae suspension 9:1 | 1.40 | 1.00 | 28.69 |
| Blueberry Juice, Algae suspension 9:1 | 2.99 | 2.02 | 32.44 |
| Water, Algae Suspension 9:1 | 2.21 | 0.59 | 73.30 |

It was observed that DHA contained in algae samples suspended in water were oxidized to a greater extent (~73.3% of the starting DHA content was oxidized) as compared to DHA contained in algae samples suspended in various juices after 6 days. Beet juice demonstrated the highest protective effect and only 11.59% of the starting DHA molecules were oxidized after incubation at 60° C. for 6 days. Juices are high in antioxidants and these bio-actives may have contributed to DHA stability in the algae samples.

Example 15

Stabilizing Algae in Juice Based Media

*S. limacinum* was inoculated into a basal medium. Equal volumes of the culture were centrifuged and the medium was decanted. The resulting algae pellets were homogenized with water at a ratio of 1:1 and individually suspended in the following mixtures at a ratio of 1:1: (i) carrot juice; (ii) beet juice; (iii) beet juice+green tea extract; (iv) blueberry juice; (v) water; (vi) water+6% sucrose (no light); or (vii) water+ 6% sucrose+green tea extract. Green tea extract was added as a source of Epigallocatechin Gallate (EGCG) which is an antioxidant polyphenol flavonoid. The water and beet juice spiked with green tea extract contained 1000 ppm of EGCG. ~0.1 gr samples were separated into aliquots, sealed in 1.5 mL tubes for determination of DHA content every 3 days for a period of 9 days. The samples were held at 60° C. Additional ~1 gr samples were separated into aliquots, sealed in the 1.5 mL tubes for determination of antioxidant activity of the mixtures every three days over a 12 day period. The samples were held at 60° C. DHA levels were quantified by gas chromatography of FAMEs, while the antioxidant content of the mixtures were determined by the DPPH (Sigma-Aldrich) analysis method in which the radical scavenging activity is presented in percentage. The results are summarized in FIGS. 10A-10B and FIGS. 11A-11B.

Figure 10A:
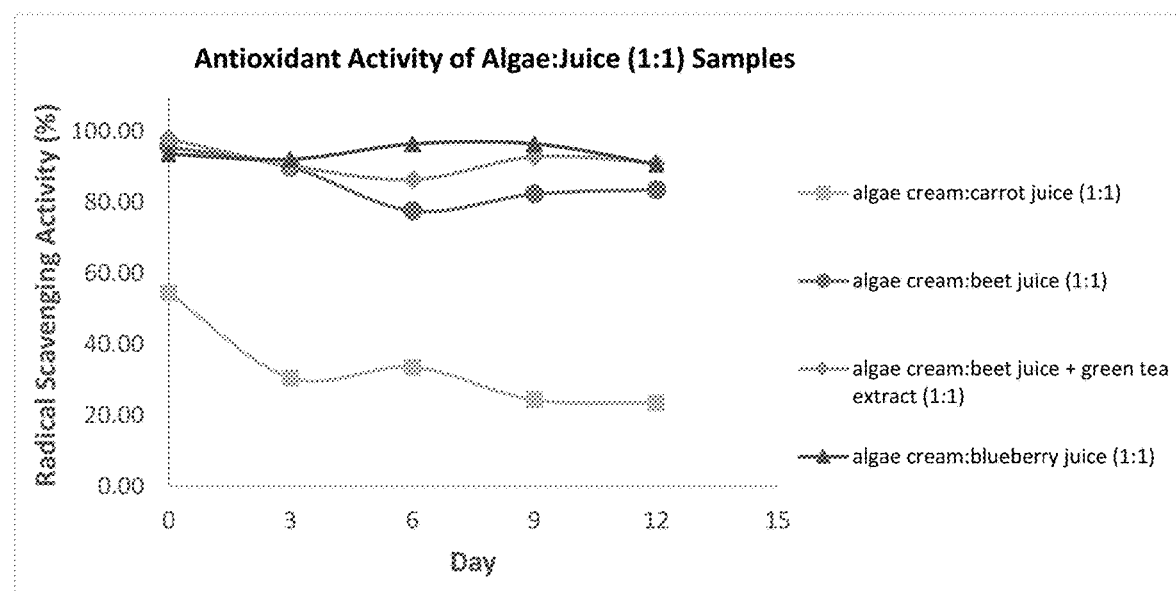
FIGS. 10A-10B are line graphs showing the radical scavenging activity (%) of algae biomass suspended in various matrices including juices.
Figure 10B:
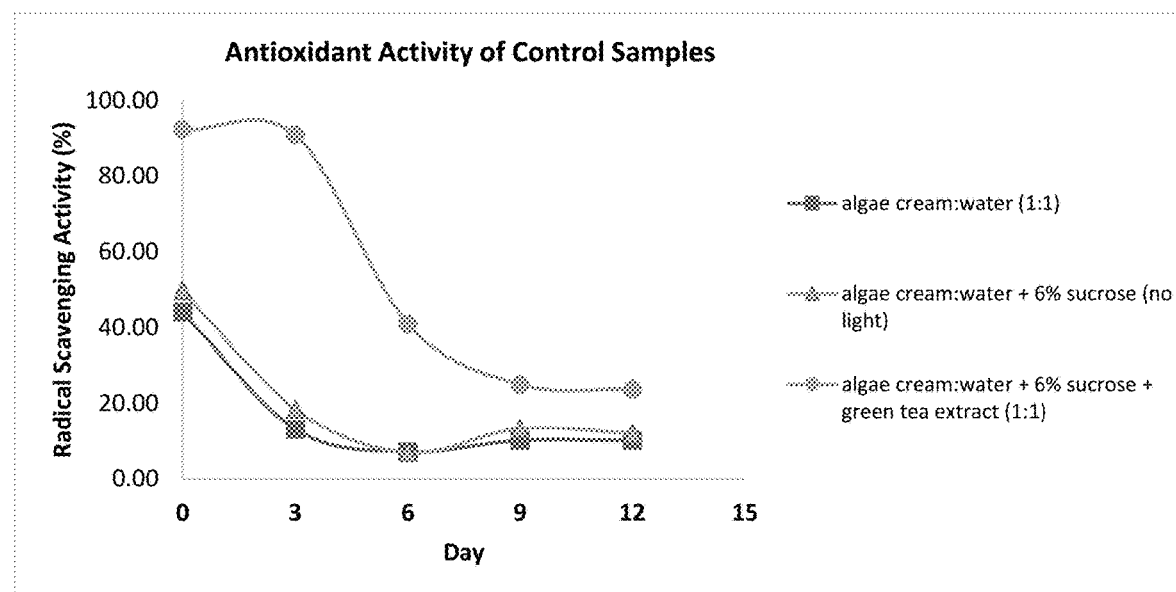
Figure 11A:
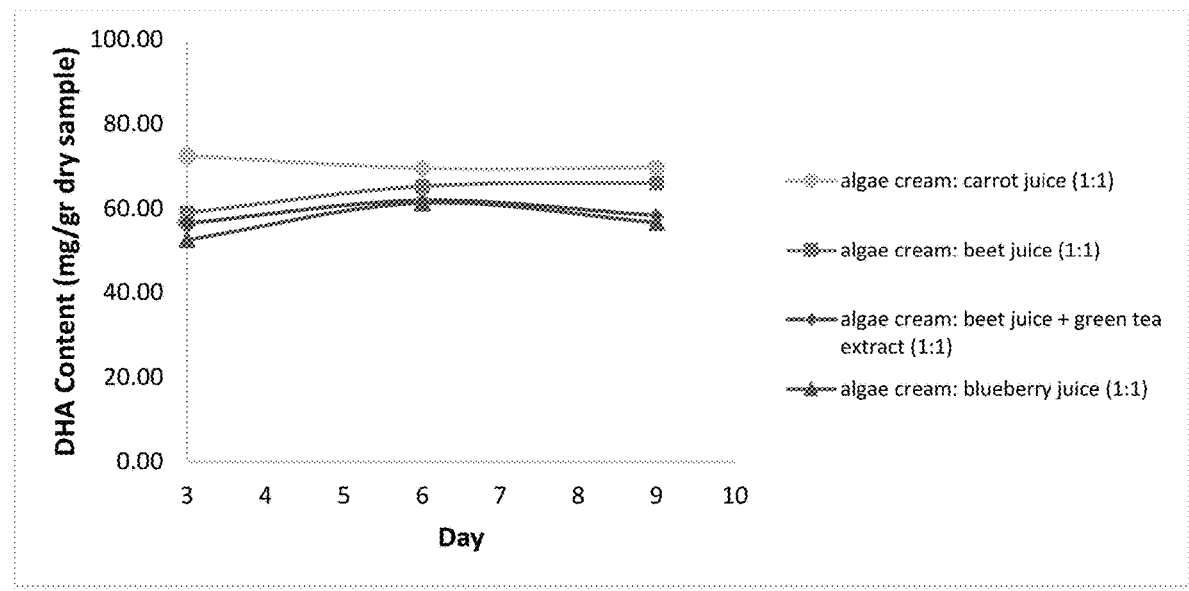
FIGS. 11A-11B are line graphs and charts showing the concentration of DHA (mg/gr dry weight) contained in algae biomass suspended in various matrices including juice.
Figure 11B:
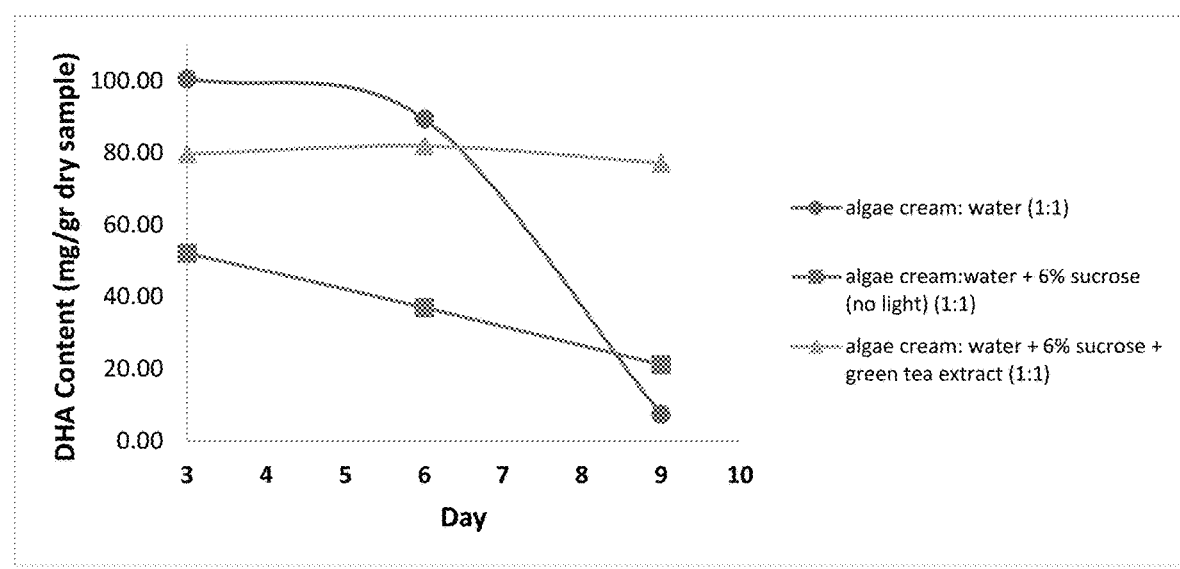

Although the algae paste has an intrinsic antioxidant activity, the addition of juices high in natural antioxidants and/or the addition of a natural antioxidant such as green tea extract extended the DHA stability under accelerated conditions. As illustrated in FIG. 10A the antioxidant activity of the algae cream mixture with beet juice, beet juice+green tea extract and blueberry juice experienced a minor decrease under accelerated temperature conditions over a 12 day period. The percentage decrease observed in the antioxidant activity of beet juice, beet juice+green tea extract and blueberry juice mixtures were only 12.6, 6.8 and 3.1%, respectively. The percentage decrease observed in the mixture of algae cream and carrot juice was higher (56.74%) as compared to the other juices, however when looking at the DHA content of the samples in FIG. 11A on day 9 a significant level of DHA loss due to oxidation was not observed which shows that the remaining antioxidants in the carrot juice were still able to prevent oxidation. On the other hand the control samples which contained algae cream and water or water containing 6% sucrose demonstrated a high level of DHA loss due to oxidation. The percentage decrease in DHA level as illustrated in FIG. 11B on day 9 in the control samples with water was found to be 92.60%. This effect might be due to the fact that the level of natural antioxidants in the algae paste alone could not stabilize the DHA under accelerated conditions and also highlights the protective effect of the juices on the stability of DHA. As presented in FIG. 10B the antioxidant activity of the control samples containing algae cream and water or water containing sucrose decreased by 77.07 and 75.83%. Fruit juices show superior antioxidant activity as compared to green tea extract alone in an algae cream background (74.9% loss); however when both green tea extract and beet juice were added to the algae cream, the antioxidant activity of the mixture proved to be more stable (6.8% loss) over 12 days.

Example 16

Algae Cream and Fruit Juices Contain Natural Antioxidants

*S. limacinum* was inoculated into a basal medium. Equal volumes of the culture were centrifuged and the medium was decanted. The resulting algae pellets were homogenized with water at a ratio of 1:1 and individually suspended in the following mixtures at a ratio of 1:1: (i) carrot juice; (ii) beet juice; (iii) blueberry juice; (iv) water. −1 gr samples were tested for antioxidant activity using the DPPH (Sigma-Aldrich) analysis method in which the radical scavenging activity is presented in percentage. These results are summarized in Table 15.

TABLE 15

| Sample | Average Radical Scavenging Activity (%) | STD | RSD (%) |
|---|---|---|---|
| algae cream:carrot juice (1:1) | 54.54 | 0.15 | 0.27 |
| algae cream:beet juice (1:1) | 95.62 | 0.87 | 0.91 |
| algae cream:blueberry juice (1:1) | 93.60 | 7.11 | 7.60 |
| algae cream:water (1:1) | 44.12 | 3.09 | 7.01 |

Algae cream demonstrated a 44.12% radical scavenging activity and the addition of juices increased the antioxidant activity of the algae cream formulation up to 95.62% in beet juice. Blueberry and carrot juice increased the radical scavenging activity % to 93.60 and 54.54, respectively.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to," and the word "comprises" has a corresponding meaning. Citation of references herein shall not be construed as an admission that such references are prior art to the present invention. The invention includes all embodiments and variations substantially as hereinbefore described and with reference to the examples and drawings.

REFERENCE

Restaino, L., Frampton, E. W., Hemphill, J. B. and Palnikar, R. (1995) "Efficacy of ozonated water against various food-related microorganisms" App. Environ. Microbiol. 61:3471-3475

Kelley, C. B. (1961) "Disinfection of sea water by ultraviolet radiation" American Journal of Public Health 51: 1670-1680

H. P. Vasantha Rupasinghe and Li Juan Yu (2012) "Emerging preservation methods for fruit juices and beverages, Food Additive, Prof. Yehia El-Samragy (Ed.), ISBN: 978-953-51-0067-6, InTech, Available from: http://www.intechopen.com/books/food-additive/emerging-preservation-methods-3-for-fruit-juices-and-beverages Shelef, G., Sukenik, A., Green, M., 1984. Microalgae Harvesting and Processing: A Literature Review. Subcontract Report, No. XK-3-03031-01. U.S. Department of Energy)

What is claimed is:

1. A method of producing an algal biomass or algal cell culture, comprising growing algae in a culture medium and harvesting the algal biomass or algal cell culture from the medium
    wherein the medium comprises juice from one or more fruits or vegetables or any combination of fruits and vegetables, a source of oxygen, and nitrogen;
    wherein the juice is aqueous liquid expressed or extracted from one or more fruits or vegetables or any combination or fruits or vegetables or puree from one or more fruits or vegetables or any combination of fruits or vegetables;
    wherein the medium is sterilized;
    wherein the nitrogen consists of natural nitrogen;
    wherein the natural nitrogen is nitrogen or sources of nitrogen that naturally occurs in and is contained in the juice; and
    wherein the medium is free from chemical additives and preservatives selected from the group consisting of corn steep liquor, nitrate, sodium nitrate, ammonia, and urea.

2. The method of claim 1, wherein the medium is supplemented with one or more of a source of salt and a source of sugar.

3. The method of claim 1, wherein the juice is selected from the group consisting of tomato juice, beet juice, carrot juice, apple juice, blueberry juice, and coconut juice.

4. The method of claim 1, wherein the algal biomass or algal cell culture is free of chemical additives and preservatives.

5. A method of producing one or more lipid compounds or compositions thereof, comprising growing algae in a medium and extracting the compound or composition from the algae,
    wherein the medium comprises juice from one or more fruits or vegetables or any combination of fruits and vegetables, a source of oxygen and nitrogen;
    wherein the juice is aqueous liquid expressed or extracted from one or more fruits or vegetables or any combination or fruits or vegetables or puree one or more fruits or vegetables or any combination of fruits or vegetables;

wherein the medium is sterilized; and wherein the nitrogen in the medium consists of natural nitrogen;

wherein the natural nitrogen is nitrogen or sources of nitrogen that naturally occurs in and is contained in the juice; and wherein the medium is free from chemical additives and preservatives selected from the group consisting of corn steep liquor, nitrate, sodium nitrate, ammonia and urea.

6. The method of claim 5, wherein the juice is selected from the group consisting of tomato juice, beet juice, carrot juice, apple juice, blueberry juice, and coconut juice.

7. The method of claim 5, wherein the lipid compound is selected from the group consisting of a polyunsaturated fatty acid, carotenoid and a fat soluble vitamin.

8. The method of claim 7, wherein the polyunsaturated fatty acid is selected from the group consisting of DHA, DPA, pinolenic acid and EPA.

9. The method of claim 8, wherein the polyunsaturated fatty acid is DHA.

10. The method of claim 8, wherein the polyunsaturated fatty acid is EPA.

11. The method of claim 5, wherein the lipid compound or composition is free of chemical additives and preservatives.

12. A method of producing a food product, cosmetic, industrial composition or pharmaceutical composition for a human or an animal, comprising the steps of:

growing algae in a culture medium and harvesting the algal biomass or algal cell culture from the medium, wherein the medium comprises juice from one or more fruits or vegetables or any combination of fruits and vegetables, a source of oxygen and nitrogen;

wherein the juice is aqueous liquid expressed or extracted from one or more fruits or vegetables or any combination or fruits or vegetables or puree from one or more fruits or vegetables or any combination of fruits or vegetables;

wherein the medium is sterilized; and wherein the nitrogen in the medium consists of natural nitrogen;

wherein the nitrogen is natural nitrogen or sources of nitrogen that naturally occurs in and is contained in the juice; and wherein the medium is free from chemical additives and preservatives selected from the group consisting of corn steep liquor, nitrate, sodium nitrate, ammonia and urea;

harvesting an algal biomass or algal cell culture from the medium;

optionally, extracting one or more lipid compounds or compositions thereof from the algal biomass or algal cell culture; and preparing the food product, industrial composition, cosmetic or pharmaceutical composition.

13. The method of claim 12, wherein a food product is prepared.

14. The method of claim 13, wherein the food product is a nutritional supplement and wherein the lipid compound is selected from the group consisting of a polyunsaturated fatty acid, carotenoid or fat soluble vitamin.

15. The method of claim 14, wherein the polyunsaturated fatty acid is selected from the group consisting of DHA, DPA, pinolenic acid and EPA.

* * * * *